United States Patent
Uyeda et al.

(10) Patent No.: US 12,319,935 B2
(45) Date of Patent: Jun. 3, 2025

(54) GENERATION OF TYPE 1 REGULATORY T CELLS THROUGH TRANSCRIPTION FACTOR TARGETING

(71) Applicant: The Board of Trustees of the Leland Stanford Junior University, Stanford, CA (US)

(72) Inventors: Molly Kathryn Javier Uyeda, Stanford, CA (US); Maria Grazia Roncarolo, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 893 days.

(21) Appl. No.: 17/430,242

(22) PCT Filed: Feb. 10, 2020

(86) PCT No.: PCT/US2020/017478
§ 371 (c)(1),
(2) Date: Aug. 11, 2021

(87) PCT Pub. No.: WO2020/167648
PCT Pub. Date: Aug. 20, 2020

(65) Prior Publication Data
US 2022/0162553 A1 May 26, 2022

Related U.S. Application Data

(60) Provisional application No. 62/806,590, filed on Feb. 15, 2019.

(51) Int. Cl.
| | | |
|---|---|---|
| A61K 39/00 | (2006.01) | |
| A61K 40/11 | (2025.01) | |
| A61K 40/22 | (2025.01) | |
| A61K 40/41 | (2025.01) | |
| A61K 40/42 | (2025.01) | |
| C12N 5/0783 | (2010.01) | |
| G01N 33/50 | (2006.01) | |
| A61K 40/50 | (2025.01) | |

(52) U.S. Cl.
CPC ............ *C12N 5/0637* (2013.01); *A61K 40/11* (2025.01); *A61K 40/22* (2025.01); *A61K 40/416* (2025.01); *A61K 40/418* (2025.01); *A61K 40/4242* (2025.01); *C12N 5/0636* (2013.01); *G01N 33/505* (2013.01); *A61K 40/50* (2025.01); *C12N 2501/60* (2013.01); *C12N 2506/45* (2013.01)

(58) Field of Classification Search
CPC ............ C12N 2510/00; C12N 2501/60; C12N 5/0636; C12N 5/0637; C12N 5/0696; A61K 39/0008; A61K 39/4611; A61K 39/464452; A61K 2039/5158; G01N 33/505; G01N 33/5073
USPC ...................................... 424/130.1
See application file for complete search history.

(56) References Cited

U.S. PATENT DOCUMENTS

2018/0125971 A1 * 5/2018 Weiner et al.
2018/0362927 A1 * 12/2018 Blazar et al.

OTHER PUBLICATIONS

Mascanfroni et al. (2015) "Metabolic control of type 1 regulatory T cell differentiation by AHR and HIF1-alpha". Nature Medicine, vol. 21, No. 6, p. 638-646.
Roncarolo et al.,(2014) "Tr1 Cells and the Counter-Regulation of Immunity: Natural Mechanisms and Therapeutic Applications". Current Topics in Microbiology and Immunology, vol. 380, pp. 39-68.

* cited by examiner

*Primary Examiner* — Robert B Mondesi
*Assistant Examiner* — Mohammad Y Meah
(74) *Attorney, Agent, or Firm* — Pamela J. Sherwood; Bozicevic, Field & Francis LLP

(57) ABSTRACT

Methods, compositions and kits for producing functional antigen-specific regulatory T cells (Tr1 cells) by reprogramming non-Tr1 target cells with suitable transcription factors.

11 Claims, 13 Drawing Sheets

Specification includes a Sequence Listing.

Differential accessibility of transcription factors between bulk T-allo10 and T-allo cells by ATAC-Seq.

| chrom | chrom Start | chrom End | nearest gene | log2FC | p-value | p adjusted |
|---|---|---|---|---|---|---|
| chr2 | 8664588 | 8665089 | ID2 | 1.59 | 0.0001 | 0.0007 |
| chr6 | 422696 | 423197 | IRF4 | 1.14 | 0.0001 | 0.0007 |
| chr15 | 61243955 | 61244456 | RORA | 1.43 | 0.0005 | 0.0038 |
| chr6 | 106094188 | 106094689 | PRDM1 | 1.01 | 0.0021 | 0.0126 |
| chr3 | 5010866 | 5011367 | BHLHE40 | 0.90 | 0.0301 | 0.1000 | chrom = chromosome
log2FC = log2 fold change (T-allo10/T-allo)
p adjusted = FDR-adjusted p value

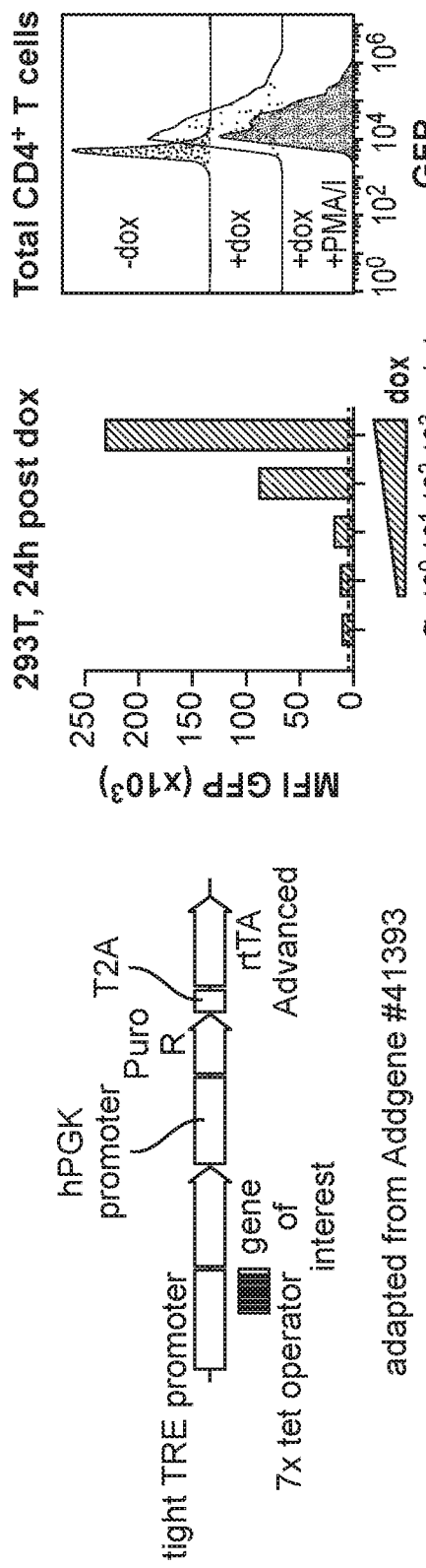
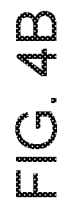
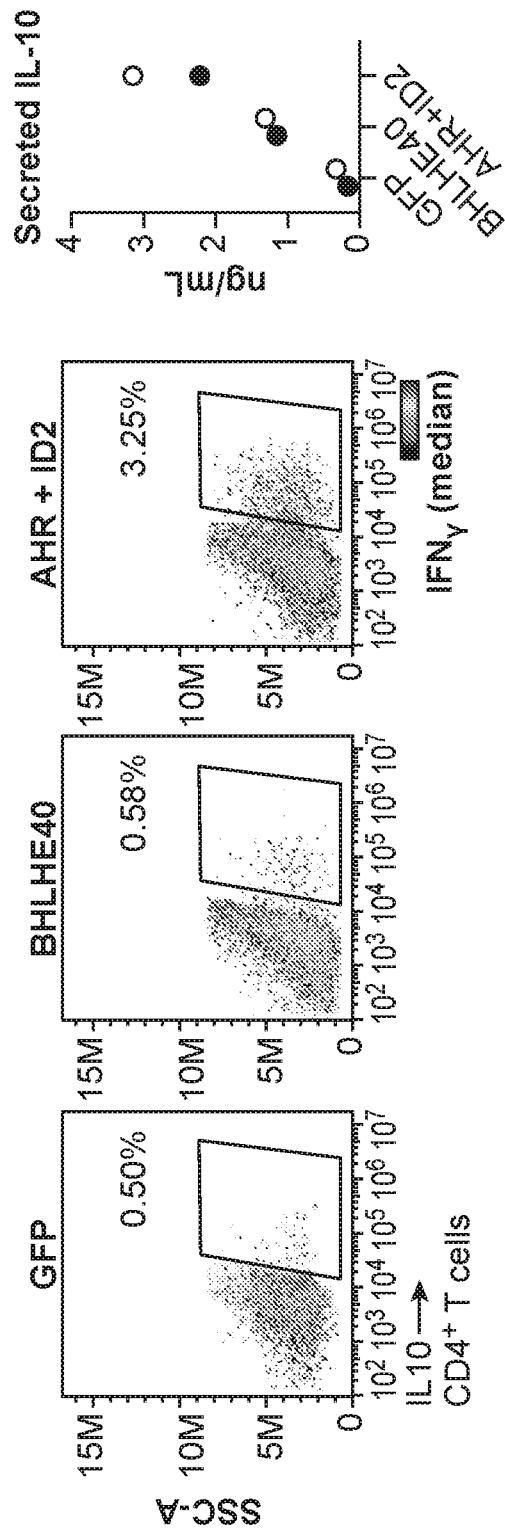
FIG. 4A
FIG. 4B
FIG. 4C

GENERATION OF TYPE 1 REGULATORY T CELLS THROUGH TRANSCRIPTION FACTOR TARGETING

CROSS REFERENCE

This application claims benefit of U.S. Provisional Patent Application No. 62/806,590, filed Feb. 15, 2019, which applications are incorporated herein by reference in their entirety.

BACKGROUND

The diverse cell types present in the adult organism are produced during development by lineage-specific transcription factors that define and reinforce cell type specific gene expression patterns. Cellular phenotypes are further stabilized by epigenetic modifications that allow faithful transmission of cell-type specific gene expression patterns over the lifetime of an organism.

Type 1 regulatory (Tr1) cells are a subset of T regulatory cells that are antigen specific and induced in the periphery. They are a tolerogenic immune subset that can suppress the activation and function of other T cells directly or indirectly through antigen presenting cells. Their specific cytokine profile of high IL-10, low/no IL-4 or IL-17, medium/high IFNγ, and variable levels of TGF-6 is a major hallmark of their functionality. Even though they play a critical role in homeostasis and diseases, their transcriptional machinery is ill defined. Unlike their thymus-derived T regulatory counterparts, Tr1 cells do not express constitutively high levels of the transcription factor FOXP3. In fact, master transcription factor(s) have not been identified for Tr1 cells, which has hindered our ability to understand their developmental trajectory. Approximately 1,600 transcription factors have been cataloged in the human genome. While some transcription factors have been identified to be involved in Tr1 cell differentiation and/or functional maintenance, there is a large disconnect between human and mouse Tr1 cells. Transcription factor evidence of mouse Tr1 cells has been generating using an IL-27 driven in vitro differentiation system that has not been established in human cells.

Identification of factors affecting the differentiation of T cells into Tr1 cells is of great interest.

PUBLICATIONS

Andolfi, et al. (2012). Enforced IL-10 expression confers type 1 regulatory T cell (Tr1) phenotype and function to human CD4+ T cells. Molecular Therapy, 20(9), 1778-1790; Bacchetta et al. (2014). Immunological outcome in haploidentical-HSC transplanted patients treated with IL-10-anergized donor T cells. Frontiers in immunology, 5, 16; Brun et al. (2009). Clinical grade production of IL-10 producing regulatory Tr1 lymphocytes for cell therapy of chronic inflammatory diseases. International immunopharmacology, 9(5), 609-613; Desreumaux et al. (2012). Safety and efficacy of antigen-specific regulatory T-cell therapy for patients with refractory Crohn's disease. Gastroenterology, 143(5), 1207-1217; "11-10-Producing Cd4+ T Cells and Uses Thereof".

Roncarolo et al. (1988). Autoreactive T cell clones specific for class I and class II HLA antigens isolated from a human chimera. J Exp Med 167, 1523-1534; Bacchetta et al. (1994). High levels of interleukin 10 production in vivo are associated with tolerance in SCID patients transplanted with HLA mismatched hematopoietic stem cells. J Exp Med 179, 493-502; Groux et al. (1997). A CD4+ T-cell subset inhibits antigen-specific T-cell responses and prevents colitis. Nature 389, 737-742; Roncarolo et al. (2018). T regulatory type 1 cells: A 30-year Journey. Immunity 49, 1004-1019.

International Application Publication No. WO20180050092; "Methods of identification and purification of human Tr1 cells using both CD49b and LAG-3 as markers and applications thereof" International Application No. WO2013192215

SUMMARY

Methods, compositions and kits for inducing Type 1 (Tr1) regulatory T cells are provided. These methods, compositions and kits find use in producing Tr1 cells for transplantation, for example to generate human in vitro induced Tr1 cells more efficiently for clinical cell therapy; to quantify and track Tr1 cells in vivo in healthy and patient individuals more accurately using intracellular markers; and to screen small molecules, biologics, and other drugs that interact with these transcription factors and can be used as an immunomodulator in immune mediated diseases and cancer. Also provided are methods, compositions and kits for screening candidate agents for activity in converting cells into Tr1 cells.

In some embodiments, methods are provided for converting a non-Tr1 target cell, for example a T cell; a hematopoietic stem cell (HSC); a lymphoid progenitor cell; a pluripotent stem cell, e.g. pPSC; etc., into induced Tr1 cells (iTr1) by contacting the target cell with a Tr1 reprogramming system comprising one or more of BHLHE40, ID2, HLF, and AHR transcription factors. In some embodiments the non-Tr1 target cell is a CD4+ T cell. In some embodiments the CD4+ T cell is a naïve T cell.

The induced expresssion of a Tr1 reprogramming system results in functional changes in the target cells, which changes include, without limitation, upregulation of IL-10 expression, reduced proliferation in response to stimulation, and expression of inhibitory molecules, e.g. LAG3, PD-1, CTLA-4, TIM-3, TIGIT, OX40, ICOS, etc. The presence of Tr1 cells may be assessed, for example, by determing the presence of cells expressinf CD49b and LAG3. In some embodiments the Tr1 reprogramming system comprises BHLHE40 alone. In some embodiments the Tr1 reprogramming system comprises ID2 and AHR in combination. In some embodiments the Tr1 reprogramming system comprises BHLHE40, ID2, and AHR.

In some embodiments iTr1 cells have antigenic specificity, that is the cells bind antigen through a T cell receptor (TCR), engineered TCR, chimeric antigen receptor (CAR), etc. to activate TCR signaling pathways. In some embodiments the antigen receptor is present and functional in the target cell prior to reprogramming, for example where the target cell is a T cell, e.g. a CD4+ T cell, etc. In other embodiments, the target cell, e.g. HSC, lymphoid progenitor cell, iPSC, etc., or iTr1 cell is engineered to express an antigen receptor, which antigen receptor may be a CAR, a TCR, etc.

In some embodiments, cells reprogrammed to be Tr1 cells, i.e. iTr1 cells, comprise genetic constructs introduced into the cell for various purposes, e.g. to increase expression of Tr1 reprogramming factors, to introduce a T cell receptor, etc. In other embodiments transcription factors may be introduced in the form of protein or mRNA, and the iTr1 is free of introduced genetic constructs.

Cell culture systems for such reprogramming methods are also provided. The cells find use in therapeutic methods, e.g.

to provide cells for therapy; in screening methods, and the like. In some embodiments, the target cells are human or mouse cells. In some embodiments, the reprogrammed population is combined with a reagent that specifically recognizes a marker associated with Tr1 cells, and cells that express the marker are selected for to provide an enriched population of Tr1 cells.

In some aspects of the invention, methods are provided for screening candidate agents for activity modulating the induction of a Tr1 phenotype. In some such embodiments, a cell culture system comprising target non-Tr1 cells, and a Tr1 reprogramming system, or an incomplete Tr1 reprogramming system (e.g. lacking one or more factors, comprising sub-optimal levels of one or more factors, and the like) is contacted with a candidate agent. The characteristics of the candidate-agent contacted cell culture system are compared with those of a cell culture system that has not been contacted with the candidate agent, where differences in the characteristics between the cell culture system that was contacted with candidate agent and the cell culture system that was not contacted with candidate agent indicate that the candidate agent modulates target cell conversion into iTr1s.

In some aspects of the invention, methods are provided for treating a subject in need of cell transplantation therapy, e.g. an individual where inhibition of an immune response is desired. Such individuals may include patients with inflammatory disorders, including without limitation autoimmune diseases such as Type 1 diabetes, multiple sclerosis, psoriasis, rheumatoid arthritis, and the like; allergies; graft versis host disease, graft rejection, etc. In some such embodiments, the subject is contacted with a composition of iTr1 cells prepared by the methods and compositions described herein. In certain embodiments, the target cells are derived from the subject, i.e. are autologous. In other embodiments the target cells are allogeneic to the subject.

In some embodiments compositions and methods are provided for treating inflammatory disease, including autoimmune inflammatory disease, particularly diseases involving inflammatory tissue, the method comprising administering to a subject (i) an effective dose of Treg cells engineered to an iTr1 phenotype; wherein the downregulate inflammatory T cell activity in an antigen-specific manner. In some embodiments, a population of iTr1 cells is provided, where the reprogramming has been performed on a non-Tr1 target cell.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2A Chromosomal location, fold change (T-allo10/T-allo) and p values of selected TFs. FIG. 2B Heat map of differentially accessible peaks in the PRDM1 region visualized using Integrated Genome Viewer. Assay for Transposase Accessible Chromatin with high-throughput sequencing (ATAC-seq) was performed as previously described on unsorted, bulk T-allo10 and T-allo samples derived from 4 independent healthy adult donors.

FIG. 4A-4C: Overexpression of BHLHE40 and AHR+ ID2 TFs leads to increased IL-10 production in expanded $CD4^+$ T cells. FIG. 4A Schematic of lentiviral overexpression vector (Addgene). TRE=tet-responsive element; PuroR=puromycin resistance element; rtTA=reverse tetracycline-controlled transactivator. FIG. 4B 293T cells transduced with the lentivirus expressing eGFP and treated with increasing doxycycline (dox; left panel). At 24 h post-dox, cells were analyzed for GFP expression by FACS at baseline or after 6 h stimulation with PMA and ionomycin (I) (right). FIG. 4C $CD4^+$ T cells transduced with indicated genes, puromycin selected, and expanded over 2 cycles were either stimulated with PMA+I for 6 h in the presence of brefeldin A and intracellular IL-10 production assessed by FACS (left panel), or stimulated for 48 h with anti-CD3/CD28 and cytokine secretion measured by ELISA (right panel). Heat map is IFNγ MFI detected with intracellular IL-10.

DETAILED DESCRIPTION

Figure 1:
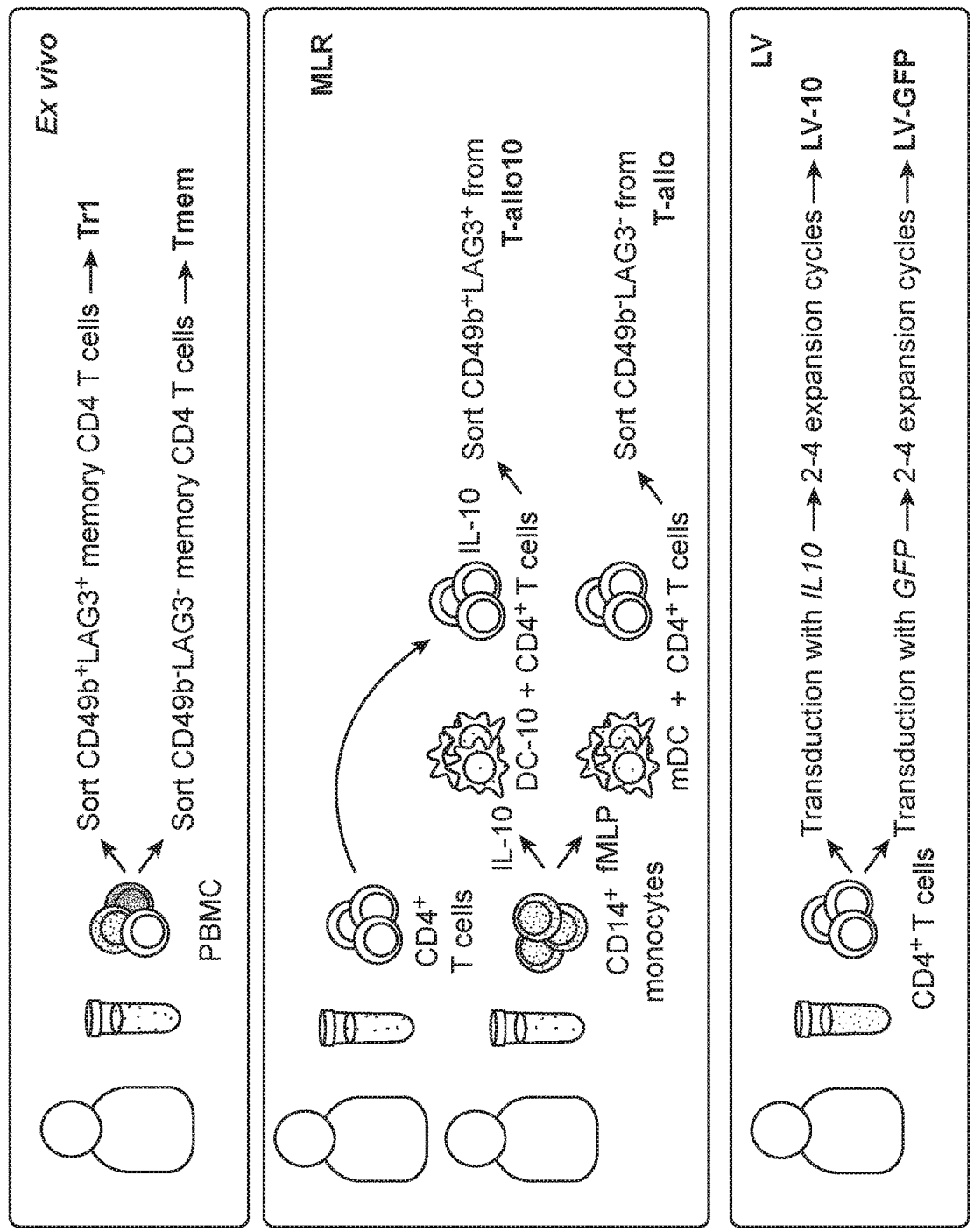
FIG. 1: Isolation and generation of 3 Tr1 subtypes and control $T_{EFF}$ cells. Top panel, ex vivo: PBMC were isolated from 3 healthy adult donors (HAD), then FACS-sorted as $CD3^+CD4^+CD45RA^-$ $CD49b^+LAG3^+$ Tr1 and $CD49b^-$ $LAG3^-$ memory T cells (Tmem) into Trizol lysis buffer for RNA extraction. Middle panel, MLR: $CD4^+$ T cells or $CD14^+$ monocytes were magnetically isolated from the PBMC of 5 HAD allogeneic pairs. Monocytes were differentiated for 7d into tolerogenic dendritic cells (DC-10) or mature DC (mDC) in the presence of IL4 and GM-CSF±IL-10 or fMLP (from d5), then co-cultured for 10d with $CD4^+$ T cells into Tr1-containing T-allo10 or control T-allo cells. Before lysis, T-allo10 were FACS-sorted for $CD49b^+$ $LAG3^+$, and T-allo cells for $CD49b^-LAG3^-$ memory $CD4^+$ T cells. Bottom panel, LV: Peripheral $CD4^+$ T cells were magnetically isolated from the PBMC of 4 HAD, stimulated for 2d with anti-CD3/CD28 and transduced with LV vector co-expressing truncated (D) NGFR and human ID10 or GFP cDNA. $DNGFR^+$ cells were sorted 12d later and expanded in 14d-cycles over irradiated allogeneic PBMC, then lysed as above.
Figures 2A, 2B:
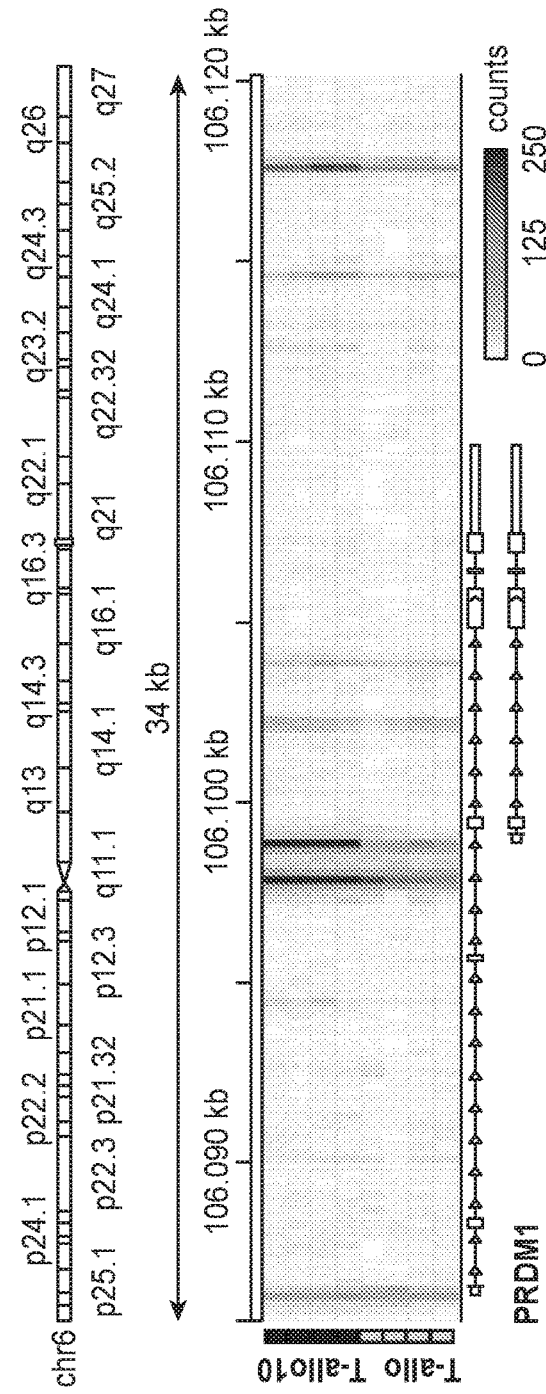
FIG. 2A-2B: Differential accessibility of candidate transcription factors (TFs) between T-allo10 and control T-allo $T_{EFF}$ cells derived by MLR.
Figure 3:
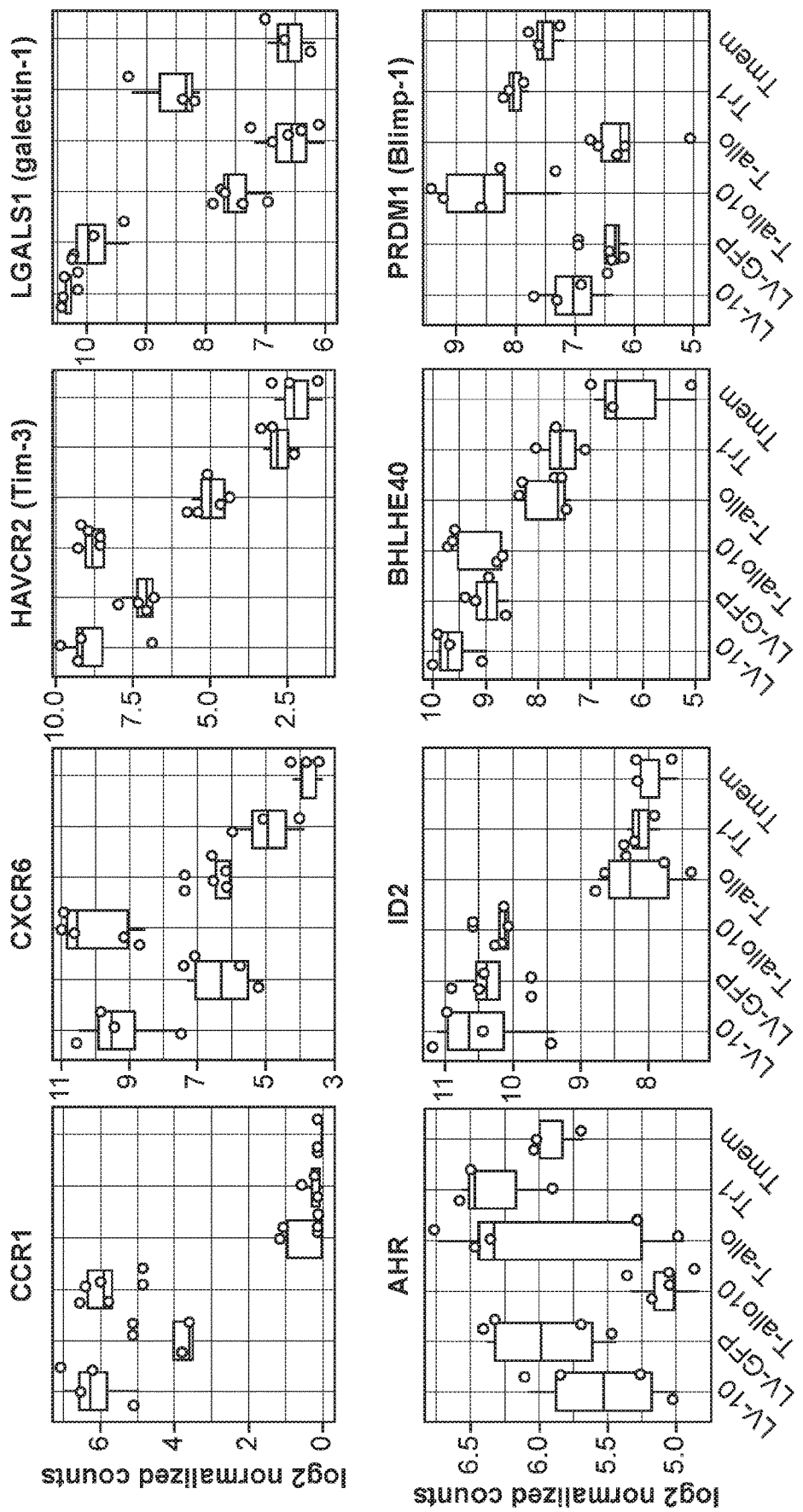
FIG. 3: mRNA expression of Tr1 biomarker candidates. mRNA of indicated genes is shown for Tr1 subtypes and control $T_{EFF}$ (LV-10 Tr1/LV-GFP, T-allo10 Tr1/T-allo, ex vivo Tr1/memory T cells (Tmem)). Box plot colors indicate surface proteiTr1 cells (yellow) or TFs (blue). Compared to control cells, CCR1, CXCR6, and HAVCR2 were significantly upregulated in LV-10 and T-allo10, BHLHE40 in T-allo10 and ex vivo, PRDM1 in T-allo10, and LGALS1 in ex vivo Tr1. Data was analyzed as described in Partek Flow. Normalized log 2-transformed counts were plotted in R (ggplot2). Boxes=interquartile range, whiskers=non-outlier range, horizontal line=median, circles=individual samples.
Figure 5:
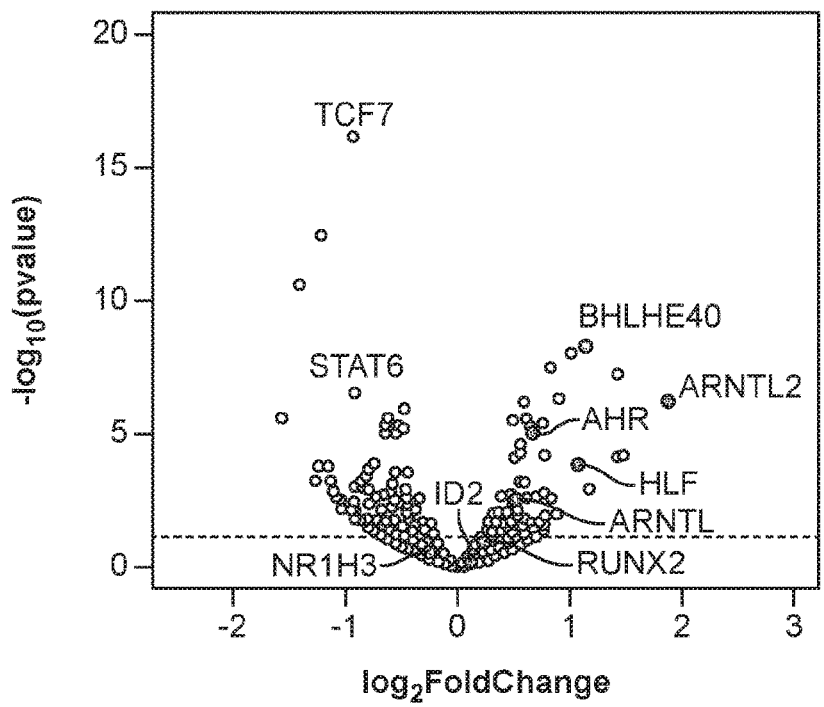
FIG. 5. 8 candidate TFs were selected from ex vivo RNA sequencing analysis. Each dot represents a detected TF (1,004 TFs plotted). Red indicates candidates from in house sequencing. Blue indicates candidates identified on IL-10 producing mouse T cells (Brockmann et al. 2018) 3 donors in biological duplicates CD3+/CD4+/CD45RA−/; Tr1: LAG3+/CD49b+; T memory: LAG3−/CD49b−
Figure 6:
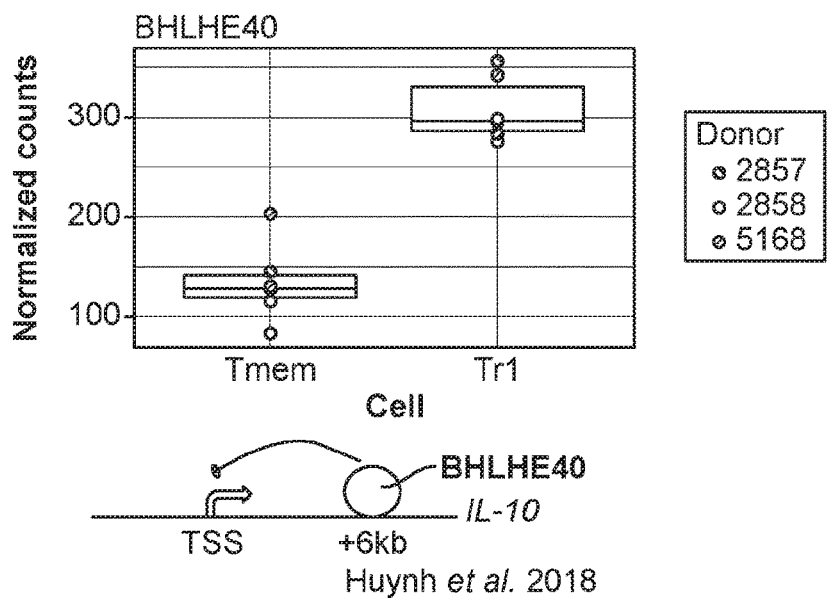
FIG. 6. In the mouse, IL-10 is upregulated and IFNγ is downregulated when BHLHE40 is knocked out. However in human Tr1 RNA seq, BHLHE40 is highly expressed.
Figure 6:
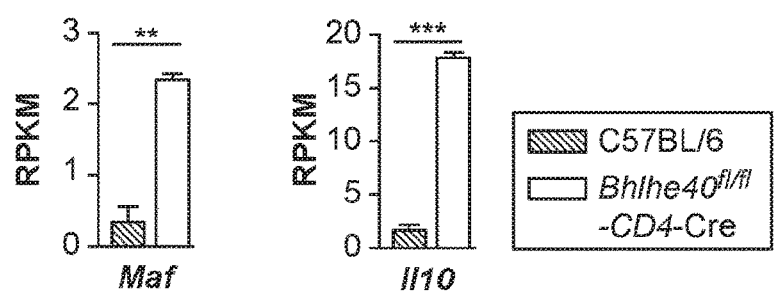
Figure 7:
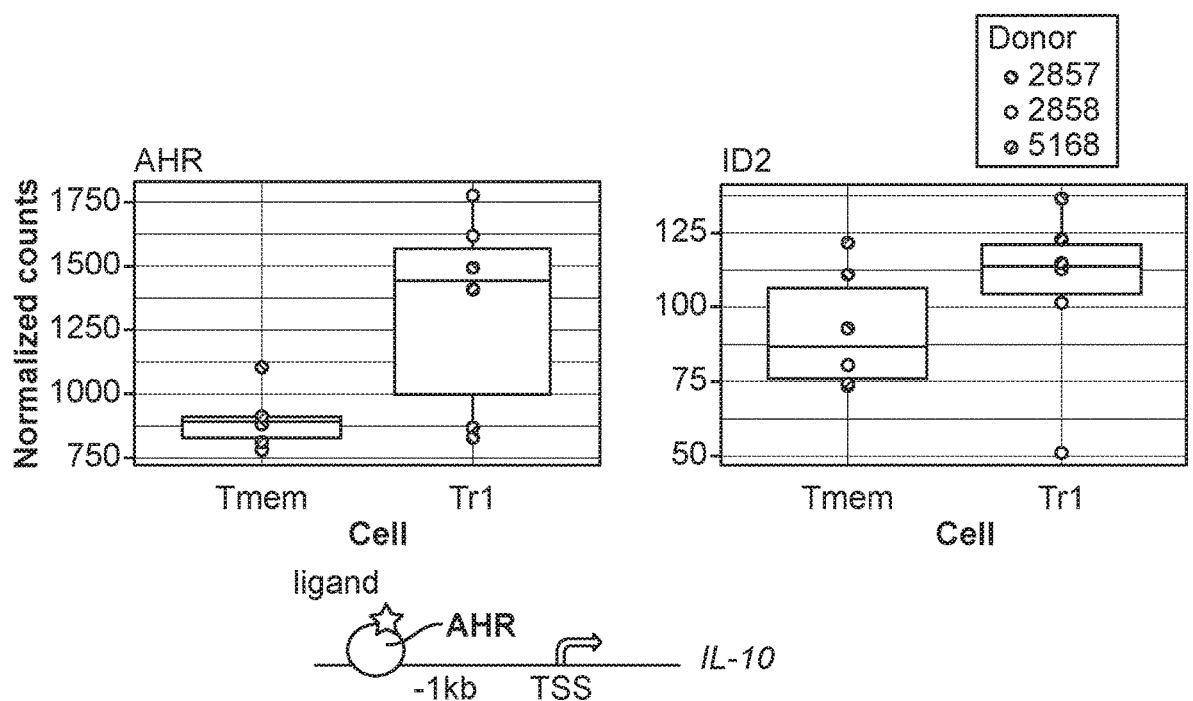
FIG. 7. AHR directly regulates IL-10 through binding to an enhancer upstream of the IL-10 TSS.
Figure 8:
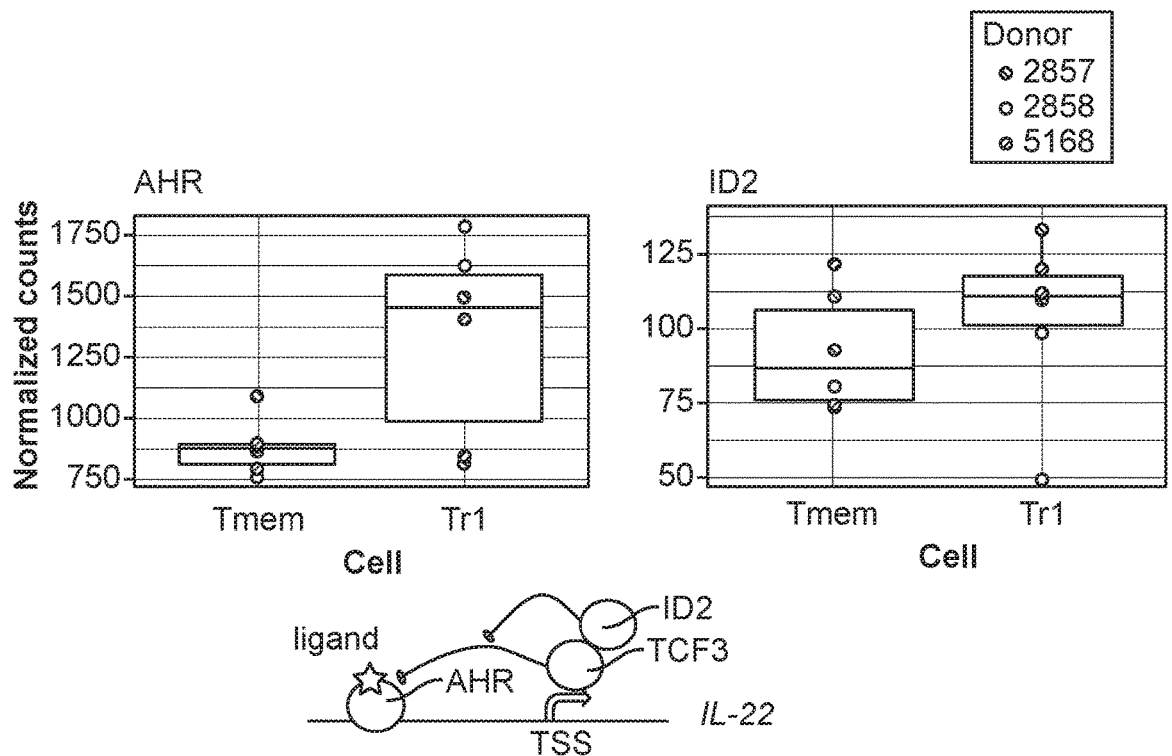
FIG. 8. AHR directly regulates IL-10 and ID2 directly interacts with an AHR inhibitor, TCF3.

Highly selective targeted T cell therapies are effective non-toxic modalities for the treatment of various conditions. Inflammatory conditions, such as RA, MS, IDDM, etc. are complex diseases where multiple elements contribute to the overall pathogenesis through both distinct and redundant mechanisms. Transforming T cells involved in the disease development to a Treg phenotype provides a specific and biologically relevant therapy.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, compositions and kits for producing a population of Tr1 cells from non-Tr1 target cells. These methods, compositions and kits find use in producing regulatory T cells for transplantation, for experimental evaluation, as a source of lineage- and cell-specific products, and the like, for example for use in treating human immune dysfunctions. Also provided are methods, compositions and kits for screening candidate agents for activity in directly converting target cells into Tr1 cells. These and other objects, advantages, and features of the invention will become apparent to those persons skilled in the art upon reading the details of the subject methods and compositions as more fully described below.

The terms "induced Tr1 cell," "iTr1 cell," encompass T cells with an antigen-specific, FoxP3⁻ regulatory T cell phenotype that arrive from a target non-Tr1 cell by experimental manipulation. Their specific cytokine profile of high IL-10, low/no IL-4 or IL-17, medium/high IFNγ, and variable levels of TGF-β is characteristic. Induced Tr1 cells express markers specific for Tr1 cells, and have functional characteristics of Tr1 regulatory T cells, that is, they inhibit immune responses in an antigen-specific manner.

The terms "Tr1 reprogramming factors" refer to one or more, i.e. a cocktail, of biologically active factors that act on a target cell to promote the reprogramming, i.e. direct conversion, of the targeted cell into a Tr1 cell. Specific factors of interest include, without limitation, one or more of BHLHE40, HLF, ID2, and AHR transcription factors. The induced expression of a Tr1 reprogramming system results in functional changes in the target cells, which changes include, without limitation, upregulation of IL-10 expression, reduced proliferation in response to stimulation, and expression of inhibitory molecules, e.g. LAG5, PD-1, CTLA-4, TIM-3, TIGIT, OX40, ICOS, etc. Quantitating the number of cells expressing one or more of such factors, alone or in combination with expression of CD49b, may be used to determine the effectiveness of reprogramming; to select for the desired cell Tr1 cells, etc.

In some embodiments the Tr1 reprogramming system comprises BHLHE40 alone. In some embodiments the Tr1 reprogramming system comprises ID2 and AHR in combination. In some embodiments the Tr1 reprogramming system comprises BHLHE40, ID2, and AHR.

The term "Tr1 reprogramming system" refers to reagents and culture conditions that promote the reprogramming of target non-Tr1 cells to induced Tr1 cells (iTr1 cells), where the target cells may be somatic cells or may be pluripotent cells. A system comprises one or more, i.e. a cocktail, of Tr1 reprogramming factors. The system may also optionally comprise other reagents, such as agents that promote cell reprogramming, agents that promote the survival and differentiation of T cells, agents that promote the differentiation of subtypes of T cells, and the like, as known in the art.

BHLHE40 (basic helix-loop-helix family member e40; MIM:604256) is a basic helix-loop-helix protein expressed in various tissues. The encoded protein can interact with ARNTL or compete for E-box binding sites in the promoter of PER1 and repress CLOCK/ARNTL's transactivation of PER1. This gene is believed to be involved in the control of circadian rhythm and cell differentiation. Refseq NP_003661.

HLF (Hepatic leukemia factor) is a member of the proline and acidic-rich (PAR) protein family, a subset of the bZIP transcription factors. The encoded protein forms homodimers or heterodimers with other PAR family members and binds sequence-specific promoter elements to activate transcription. Chromosomal translocations fusing portions of this gene with the E2A gene cause a subset of childhood B-lineage acute lymphoid leukemias. Alternatively spliced transcript variants have been described, but their biological validity has not been determined. Refseq NP_002117.

AHR (aryl hydrocarbon receptor) is a member of the family of basic helix-loop-helix transcription factors. AHR binds several exogenous ligands such as natural plant flavonoids, polyphenolics and indoles, as well as synthetic polycyclic aromatic hydrocarbons and dioxin-like compounds. AhR is a cytosolic transcription factor that is normally inactive, bound to several co-chaperones. Upon ligand binding to chemicals such as 2,3,7,8-tetrachlorodibenzo-p-dioxin (TCDD), the chaperones dissociate resulting in AhR translocating into the nucleus and dimerizing with ARNT (AhR nuclear translocator), leading to changes in gene transcription. The AhR protein contains several domains critical for function and is classified as a member of the basic helix-loop-helix/Per-Arnt-Sim (bHLH/PAS) family of transcription factors. The bHLH motif is located in the N-terminal of the protein and is a common entity in a variety of transcription factors. Members of the bHLH superfamily have two functionally distinctive and highly conserved domains. The first is the basic-region (b), which is involved in the binding of the transcription factor to DNA. The second is the helix-loop-helix (HLH) region, which facilitates protein-protein interactions. Also contained with the AhR are two PAS domains, PAS-A and PAS-B, which are stretches of 200-350 amino acids that exhibit a high sequence homology to the protein domains that were originally found in the *Drosophila* genes period (Per) and single-minded (Sim) and in AhR's dimerization partner the aryl hydrocarbon receptor nuclear translocator (ARNT). The PAS domains support specific secondary interactions with other PAS domain containing proteins, as is the case with AhR and ARNT, so that dimeric and heteromeric protein complexes can form. The ligand binding site of AhR is contained within the PAS-B domain[12] and contains several conserved residues critical for ligand binding.[13] Finally, a glutamine-rich (Q-rich) domain is located in the C-terminal region of the protein and is involved in co-activator recruitment and transactivation. Refseq NP_001612.

ID2 (DNA-binding protein inhibitor) belongs to the inhibitor of DNA binding (ID) family, members of which are transcriptional regulators that contain a helix-loop-helix (HLH) domain but not a basic domain. Members of the ID family inhibit the functions of basic helix-loop-helix transcription factors in a dominant-negative manner by suppressing their heterodimerization partners through the HLH domains. This protein may play a role in negatively regulating cell differentiation. Refseq NP_002157.

Regulatory T cells. Regulatory T cells ("Treg") are a specialized subpopulation of T cells which suppresses activation of the immune system and thereby maintains tolerance to self-antigens. These include natural regulatory T cells (nTreg), which are T cells produced in the thymus and delivered to the periphery as a long-lived lineage of self-antigen-specific lymphocytes; and induced regulatory T cells (iTreg), which are recruited from circulating lymphocytes and acquire regulatory properties under particular conditions of stimulation in the periphery. Both cell types are CD4+CD25+, both can inhibit proliferation of CD4+ CD25− T cells in a dose dependent manner, and both are anergic and do not proliferate upon TCR stimulation. In addition to being positive for CD4 and CD25, regulatory T cells are positive for the transcription factor Foxp3, an intracellular marker.

Tr1 cells are memory $CD4^+$ T cells that co-express the integrin alpha2 subunit (CD49b) and the lymphocyte-activation gene 3 (LAG-3). Although other cell surface markers, including PD-1, ICOS, TIGIT, CD39, CD73, TIM-3, GITR, OX40, TNFRSF9, and CEACAM-1, have been associated with Tr1 cells, their expression on other cell types precludes them from being defined as Tr1-specific markers. Tr1 cells produce high levels of IL-10 and TGF-ß; variable amounts of IFN-γ; and low/no IL-2, IL-4, and IL-17 and have a specific gene signature. In addition, Tr1 cells have unique metabolic requirements that distinguish them from $FOXP3^+$ Tregs: Tr1 cells depend on glycolysis and are inhibited by hypoxia and extracellular ATP, while peripheral $FOXP3^+$ Tregs depend on fatty acid oxidation.

The main mechanism of Tr1-mediated suppression is the secretion of IL-10 and TGF-$\beta$. Importantly, Tr1 cells require activation via their T cell receptor, thus by their cognate antigen (Ag), to mediate suppression, but, once activated, they mediate bystander suppression against other Ags. The expression of granzyme (Gz) B endows Tr1 cells with the ability to specifically kill myeloid APCs. Similar to $FOXP3^+$ Tregs, Tr1 cells also inhibit T cell responses via CTLA-4/CD80 and PD-1/PDL-1 interactions and metabolic disruption. IL-10 signaling is required for maintaining high IL-10 production by Tr1 cells, which in turn is necessary for controlling inflammatory responses. Notably, in the absence of IL-10-mediated signaling, Tr1 cells lose their ability to secrete IL-10, but they still express GzB and CTLA-4. These findings suggest that in the absence of IL-10/IL-10R-mediated signaling, and consequent IL-10 production, Tr1 cells may suppress immune responses via alternative mechanisms such as specific killing of APCs and/or cell-to-cell contact-mediated inhibition of effector T cells and APCs.

A defect in Tr1 cell frequency/function has been consistently demonstrated in a number of autoimmune and inflammatory diseases in preclinical and clinical models, indicating that IL-10-producing Tr1 cells are relevant for disease protection. These evidences built the rationale for medical intervention for Tr1 cell boosting in vivo to prevent/cure T cell-mediated diseases, for example autoimmune diseases, including type 1 diabetes (T1 D) and multiple sclerosis (MS). T regulatory type 1 cells have been associated with long-term transplantation tolerance, induced or spontaneously established, in preclinical and clinical settings. In vitro induced Tr1 cells can be used as cellular therapy to treat inflammatory and autoimmune disease as well as to control graft-versus-host disease (GvHD) and to prevent organ rejection.

In some embodiments, methods of engineering and expanding Tr1 cells are employed to produce an enriched population of engineered Tr1 cells. By an "enriched population", it is meant that the representation of Tr1 cells in the cell population is greater than would otherwise be, e.g., in the absence of the methods provided. In other words, methods of the invention increase the percentage of regulatory T cells in the population by at least 1.5 fold or more, e.g. 2-fold or more, in some instances 3-fold or more, relative to the number of regulatory T cells that would exist in the cell population in the absence of enrichment.

In some embodiments, the target non-Tr1 cells comprise a complex mixture of immune cells, e.g., peripheral blood lymphocytes, lymph node samples, T cell samples from sites of autoimmune lesions, and the like. Such cells may be, for example, obtained from an individual that will be treated with the engineered cells.

In other embodiments, a target T cell for reprogramming is allogeneic with respect to the individual will be treated. A universal 'off the shelf' T cell product provides advantages in uniformity of harvest and manufacture.

In addition to modifying T cells, induced pluripotent stem (iPS) T cells can provide a source of allogeneic cells. For example, transducing donor T cells with reprogramming factors can restore pluripotency, and are then re-differentiated to T effector cells.

T cells for reprogramming as described above collected from a subject or a donor may be separated from a mixture of cells by techniques that enrich for desired cells, or may be engineered and cultured without separation. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody, e.g., complement and cytotoxic cells, and "panning" with antibody attached to a solid matrix, e.g., a plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintain Tr1 cells the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum (FCS).

The collected and optionally enriched cell population may be used immediately for genetic modification, or may be frozen at liquid nitrogen temperatures and stored, being thawed and capable of being reused. The cells will usually be stored in 10% DMSO, 50% FCS, 40% RPMI 1640 medium.

The reprogrammed cells may be infused to the subject in any physiologically acceptable medium by any convenient route of administration, normally intravascularly, although they may also be introduced by other routes, where the cells may find an appropriate site for growth. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of T cells that are obtained during collection. Optionally the reprogrammed cells are selected for expression of LAG3 and CD49b prior to use.

Expression construct: The reprograming factor coding sequence may be introduced on an expression vector into a cell to be engineered. For example, a reprogramming factor coding sequence may be introduced into a target cell using CRISPR technology. CRISPR/Cas9 system can be directly applied to human cells by transfection with a plasmid that encodes Cas9 and sgRNA. The viral delivery of CRISPR components has been extensively demonstrated using lentiviral and retroviral vectors. Gene editing with CRISPR encoded by non-integrating virus, such as adenovirus and adenovirus-associated virus (AAV), has also been reported. Recent discoveries of smaller Cas proteins have enabled and enhanced the combination of this technology with vectors that have gained increasing success for their safety profile and efficiency, such as AAV vectors.

The nucleic acid encoding a reprograming factor is inserted into a vector for expression and/or integration. Many such vectors are available. The vector components generally include, but are not limited to, one or more of the following: an origin of replication, one or more marker genes, an enhancer element, a promoter, and a transcription termination sequence. Vectors include viral vectors, plasmid vectors, integrating vectors, and the like.

Expression vectors may contain a selection gene, also termed a selectable marker. This gene encodes a protein necessary for the survival or growth of transformed host cells grown in a selective culture medium or a truncated gene encoding a surface marker that allows for antibody based detection. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, or (d) enable surface antibody based detection for isolation via fluoresences activating cell sorting (FACS) or magnetic separation e.g. truncated forms of NGFR, EGFR, CD19.

Nucleic acids are "operably linked" when placed into a functional relationship with another nucleic acid sequence. For example, DNA for a signal sequence is operably linked to DNA for a polypeptide if it is expressed as a preprotein that signals the secretion of the polypeptide; a promoter or enhancer is operably linked to a coding sequence if it affects the transcription of the sequence; and a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Expression vectors will contain a promoter that is recognized by the host organism and is operably linked to the ABD construct coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus LTR (such as murine stem cell virus), hepatitis-B virus and Simian Virus 40 (SV40), from heterologous mammalian promoters, e.g., the actin promoter, PGK (phosphoglycerate kinase), or an immunoglobulin promoter, or from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes may be increased by inserting an enhancer sequence into the vector. Enhancers are cis-acting elements of DNA, usually about from 10 to 300 bp in length, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors for use in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

Suitable host cells for cloning a construct are the prokaryotic, yeast, or other eukaryotic cells described above. Examples of useful mammalian host cell lines are mouse L cells (L-M[K-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse Sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells, including T cells, stem cells, etc. can be transfected with the above-described expression vectors for construct expression. Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "sequence identity," as used herein in reference to polypeptide or DNA sequences, refers to the subunit sequence identity between two molecules. When a subunit position in both of the molecules is occupied by the same monomeric subunit (e.g., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990).

By "protein variant" or "variant protein" or "variant polypeptide" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild-type (or native) polypeptide, or a variant or engineered version of a wild-type polypeptide. Parent polypeptide may refer to the polypeptide itself, compositions that comprise the parent polypeptide, or the amino acid sequence that encodes it.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogs" refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acid modifications disclosed herein may include amino acid substitutions, deletions and insertions, particularly amino acid substitutions. Variant proteins may also include conservative modifications and substitutions at other positions of the cytokine and/or receptor (e.g., positions other than those involved in the affinity engineering). Such conservative substitutions include those described by Dayhoff in The Atlas of Protein Sequence and Structure 5 (1978), and by Argos in EMBO J., 8:779-785 (1989). For example, amino acids belonging to one of the following groups represent conservative changes: Group I: Ala, Pro, Gly, Gln, Asn, Ser, Thr; Group II: Cys, Ser, Tyr, Thr; Group III: Val, Ile, Leu, Met, Ala, Phe; Group IV: Lys, Arg, His; Group V: Phe, Tyr, Trp, His; and Group VI: Asp, Glu. Further, amino acid substitutions with a designated amino acid may be replaced with a conservative change.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99% or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In some embodiments, the mammal is a human. The terms "subject," "individual," and "patient" encompass, without limitation, individuals having a disease. Subjects may be human, but also include other mammals, particularly those mammals useful as laboratory models for human disease, e.g., mice, rats, etc.

The term "sample" with reference to a patient encompasses blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

The term "diagnosis" is used herein to refer to the identification of a molecular or pathological state, disease or condition in a subject, individual, or patient.

The term "prognosis" is used herein to refer to the prediction of the likelihood of death or disease progression, including recurrence, spread, and drug resistance, in a subject, individual, or patient. The term "prediction" is used herein to refer to the act of foretelling or estimating, based on observation, experience, or scientific reasoning, the likelihood of a subject, individual, or patient experiencing a particular event or clinical outcome. In one example, a physician may attempt to predict the likelihood that a patient will survive.

As used herein, the terms "treatment," "treating," and the like, refer to administering an agent, or carrying out a procedure, for the purposes of obtaining an effect on or in a subject, individual, or patient. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of cancer in a mammal, particularly in a human, and includes: (a) inhibiting the disease, i.e., arresting its development; and (b) relieving the disease or its symptoms, i.e., causing regression of the disease or its symptoms.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of engineered cells to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

As used herein, a "therapeutically effective amount" refers to that amount of the therapeutic agent, e.g. an infusion of engineered T cells, etc., sufficient to treat or manage a disease or disorder. A therapeutically effective amount may refer to the amount of therapeutic agent sufficient to delay or minimize the onset of disease, e.g., to delay or minimize the growth and spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"In combination with", "combination therapy" and "combination products" refer, in certain embodiments, to the concurrent administration to a patient of the engineered proteins and cells described herein in combination with additional therapies, e.g. surgery, radiation, chemotherapy, and the like. When administered in combination, each component can be administered at the same time or sequentially in any order at different points in time. Thus, each component can be administered separately but sufficiently closely in time so as to provide the desired therapeutic effect.

"Concomitant administration" means administration of one or more components, such as engineered proteins and cells, known therapeutic agents, etc. at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Chimeric antigen receptor (CAR). A CAR is comprised of the general structure where an antigen binding domain, usually provided in an scFv format, is linked to T cell receptor effector functions. The term refers to artificial multi-module molecules capable of triggering or inhibiting the activation of an immune cell. A CAR will generally comprise an antigen binding domain, linker, transmembrane domain and cytoplasmic signaling domain. In some instances, a CAR will include one or more co-stimulatory domains and/or one or more co-inhibitory domaiTr1 cells.

A spacer region links the antigen binding domain to the transmembrane domain. It should be flexible enough to allow the antigen binding domain to orient in different directions to facilitate antigen recognition. The simplest form is the hinge region from an immunoglobulin, e.g. the hinge from any one of IgG1, IgG2a, IgG2b, IgG3, IgG4, particularly the human protein sequences. Alternatives include the CH2CH3 region of immunoglobulin and portions of CD3. For many scFv based constructs, an IgG hinge is effective.

The CAR transmembrane domain (TM) is frequently derived from type I membrane proteiTr1 cells, such as CD3, CD4, CD8, CD28, etc.

A cytoplasmic signaling domain, such as those derived from the T cell receptor ζ-chain, is employed as part of the CAR in order to produce stimulatory signals for T lymphocyte proliferation and effector function following engagement of the chimeric receptor with the target antigen. Endodomains from co-stimulatory molecules may be included in the cytoplasmic signaling portion of the CAR.

The term "co-stimulatory domain", refers to a stimulatory domain, typically an endodomain, of a CAR that provides a secondary non-specific activation mechanism through which a primary specific stimulation is propagated. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies. Nat Rev Immunol (2013) 13(4):227-42, the disclosure of which are incorporated herein by reference in their entirety. Non-limiting examples of suitable co-stimulatory polypeptides include, but are not limited to, 4-1BB (CD137), CD28, ICOS, OX-40, BTLA, CD27, CD30, GITR, and HVEM.

The term "co-inhibitory domain" refers to an inhibitory domain, typically an endodomain, derived from a receptor that provides secondary inhibition of primary antigen-specific activation mechanisms which prevents co-stimulation. Co-inhibition, e.g., T cell co-inhibition, and the factors involved have been described in Chen & Flies. *Nat Rev Immunol* (2013) 13(4):227-42 and Thaventhiran et al. *J Clin Cell Immunol* (2012) S12. In some embodiments, co-inhibitory domaiTr1 cells homodimerize. A co-inhibitory domain can be an intracellular portion of a transmembrane protei. Non-limiting examples of suitable co-inhibitory polypeptides include, but are not limited to, CTLA-4 and PD-1.

A first-generation CAR transmits the signal from antigen binding through only a single signaling domain, for example a signaling domain derived from the high-affinity receptor for IgE FcERIy, or the CD3 chain. The domain contains one or three immunoreceptor tyrosine-based activating motif(s) [ITAM(s)] for antigen-dependent T-cell activation. The ITAM-based activating signal endows T-cells with the ability to lyse the target tumor cells and secret cytokines in response to antigen binding.

Second-generation CARs include a co-stimulatory signal in addition to the CD3 signal. Coincidental delivery of the delivered co-stimulatory signal enhances cytokine secretion and antitumor activity induced by CAR-transduced T-cells. The co-stimulatory domain is usually be membrane proximal relative to the CD3 domain. Third-generation CARs include a tripartite signaling domain, comprising for example a CD28, CD3, OX40 or 4-1BB signaling region. In fourth generation, or "armored car" CAR T-cells are further gene modified to express or block molecules and/or receptors to enhance immune activity.

CAR variants include split CARs wherein the extracellular portion, the ABD and the cytoplasmic signaling domain of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR molecules and derivatives thereof (i.e., CAR variants) are described, e.g., in PCT Application Nos. US2014/016527, US1996/017060, US2013/063083; Fedorov et al.

Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

CAR variants also include bispecific or tandem CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. Tandem CARs (TanCAR) mediate bispecific activation of T cells through the engagement of two chimeric receptors designed to deliver stimulatory or costimulatory signals in response to an independent engagement of two different tumor associated antigens. iCARs use the dual antigen targeting to shout down the activation of an active CAR through the engagement of a second suppressive receptor equipped with inhibitory signaling domaiTr1 cells The dual recognition of different epitopes by two CARs diversely designed to either deliver killing through ζ-chain or costimulatory signals, e.g. through CD28 allows a more selective activation of the reprogrammed T cells by restricting Tandem CAR's activity to cancer cell expressing simultaneously two antigens rather than one. The potency of delivered signals in engineered T cells will remain below threshold of activation and thus ineffective in absence of the engagement of costimulatory receptor. The combinatorial antigen recognition enhances selective tumor eradication and protects normal tissues expressing only one antigen from unwanted reactions.

Inhibitory CARs (iCARs) are designed to regulate CAR-T cells activity through inhibitory receptors signaling modules activation. This approach combines the activity of two CARs, one of which generates dominant negative signals limiting the responses of CAR-T cells activated by the activating receptor. iCARs can switch off the response of the counteracting activator CAR when bound to a specific antigen expressed only by normal tissues. In this way, iCARs-T cells can distinguish cancer cells from healthy ones, and reversibly block functionalities of transduced T cells in an antigen-selective fashion. CTLA-4 or PD-1 intracellular domaiTr1 cells in iCARs trigger inhibitory signals on T lymphocytes, leading to less cytokine production, less efficient target cell lysis, and altered lymphocyte motility.

Methods

The subject invention is directed to methods of reprogramming target cell with a reprogramming system comprising one or more Tr1 cell reprogramming factor. Tr1 reprogramming factors are biologically active factors that act on a cell to alter transcription so as to convert the cell into a regulatory Tr1 cells. These factors are provided to cells in the context of a system, e.g. an in vitro culture system.

Examples of NR factors include an BHLHE40 agent, an ID2 agent, and an AHR agent. In certain embodiments, particularly for human cells, Tr1 reprogramming factors may comprise all three of these agents, may comprise any two of the agents, e.g. an ID2 agent, and an AHR agent, and may comprise a single agent, e.g. a BHLHE40 agent.

The term BHLHE40 agent is used to refer to BHLHE40 polypeptides and the nucleic acids that encode them. BHLHE40 is a transcription factor, basic helix-loop-helix family member e40. The human reference sequence for mRNA may be accessed at Genbank NM_003670 and the reference protein at NP_003661. The terms "BHLHE40 gene product", "BHLHE40 polypeptide", and "BHLHE40 protein" are used interchangeably herein to refer to native sequence BHLHE40 polypeptides, BHLHE40 polypeptide variants, BHLHE40 polypeptide fragments and chimeric BHLHE40 polypeptides that can modulate transcription. Native sequence BHLHE40 polypeptides include the protein BHLHE40. BHLHE40 polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the BHLHE40 agent is BHLHE40 protein.

The term ID2 agent is used to refer to ID2 polypeptides and the nucleic acids that encode them. ID2 is a transcription factor, inhibitor of DNA binding 2. The human reference sequence for mRNA may be accessed at Genbank NM_002166 and the reference protein at NP_002157. The terms "ID2 gene product", "ID2 polypeptide", and "ID2 protein" are used interchangeably herein to refer to native sequence ID2 polypeptides, ID 2 polypeptide variants, ID2 polypeptide fragments and chimeric ID2 polypeptides that can modulate transcription. Native sequence ID2 polypeptides include the protein ID2. ID2 polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the ID2 agent is ID2 protein.

The term AHR agent is used to refer to AHR polypeptides and the nucleic acids that encode them. AHR is a transcription factor, aryl hydrocarbon receptor. The human reference sequence for mRNA may be accessed at Genbank NM_001621 and the reference protein at NP_001612. The terms "AHR gene product", "AHR polypeptide", and "AHR protein" are used interchangeably herein to refer to native sequence AHR polypeptides, ID 2 polypeptide variants, AHR polypeptide fragments and chimeric AHR polypeptides that can modulate transcription. Native sequence AHR polypeptides include the protein AHR. AHR polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the AHR agent is AHR protein.

In some embodiments, the one or more reprogramming factors are provided as nuclear acting polypeptides. In other words, the subject cells are contacted with reprogramming polypeptides that act in the nucleus.

To promote transport of reprogramming polypeptides across the cell membrane, reprogramming polypeptide sequences may be fused to a polypeptide permeant domain. A number of permeant domains are known in the art and may be used in the nuclear acting polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The reprogramming polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Other methods of preparing polypeptides in a cell-free system include, for example, those methods taught in U.S. Application Ser. No. 61/271,000, which is incorporated herein by reference.

The reprogramming polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. reprogramming polypeptides may be produced recombinantly not only directly, but also as a fusion polypeptide with a heterologous polypeptide, e.g. a polypeptide having a specific cleavage site at the N-terminus of the mature protein or polypeptide. Expression vectors usually contain a selection gene, also termed a selectable marker. This gene encodes a protein necessary for the survival or growth of transformed host cells grown in a selective culture medium.

Following purification by commonly known methods in the art, reprogramming polypeptides are provided to the subject cells by standard protein transduction methods. In some cases, the protein transduction method includes contacting cells with a composition containing a carrier agent and at least one purified reprogramming polypeptide. Examples of suitable carrier agents and methods for their use include, but are not limited to, commercially available reagents such as Chariot™ (Active Motif, Inc., Carlsbad, Calif.) described in U.S. Pat. No. 6,841,535; Bioport™ (Gene Therapy Systems, Inc., San Diego, Calif.), GenomeONE (Cosmo Bio Co., Ltd., Tokyo, Japan), and Proteo-Juice™ (Novagen, Madison, Wis.), or nanoparticle protein transduction reagents as described in, e.g., U.S. patent application Ser. No. 10/138,593.

In other embodiments, the one or more reprogramming factors are nucleic acids encoding reprogramming polypeptides, i.e. reprogramming nucleic acids. Vectors used for providing reprogramming nucleic acids to the subject cells will typically comprise suitable promoters for driving the expression, that is, transcriptional activation, of the nucleic acids. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10-fold, by at least about 100-fold, more usually by at least about 1000-fold. In addition, vectors used for providing the nucleic acids may include genes that must later be removed, e.g. using a recombinase system such as Cre/Lox, or the cells that express them destroyed, e.g. by including genes that allow selective toxicity such as herpesvirus TK, bcl-xs, etc Reprogramming nucleic acids may be provided directly to the subject cells. In other words, the cells are contacted with vectors comprising reprogramming nucleic acids such that the vectors are taken up by the cells. Methods for contacting cells with nucleic acid vectors, such as electroporation, calcium chloride transfection, and lipofection, are well known in the art. Vectors that deliver nucleic acids in this manner are usually maintained episomally, e.g. as plasmids or minicircle DNAs.

Alternatively, the nucleic acid may be provided to the subject cells via a virus. In other words, the cells are contacted with viral particles comprising the reprogramming nucleic acids. Retroviruses, for example, lentiviruses, are particularly suitable to such methods. Commonly used retroviral vectors are "defective", i.e. unable to produce viral proteiTr1 cells required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteiTr1 cells are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject cells are targeted by the packaged viral particles. Methods of introducing the retroviral vectors comprising reprogramming nucleic acids into packaging cell lines and of collecting the viral particles that are generated by the packaging lines are well known in the art.

When more than one reprogramming factors is provided, the reprogramming factors may be provided individually or as a single composition, that is, as a premixed composition, of factors. The reprogramming factors may be added to the subject cells simultaneously or sequentially at different times. reprogramming factors may be provided to target cells individually or as a single composition, that is, as a premixed composition, of reprogramming factors. The factors may be provided at the same molar ratio or at different molar ratios. The factors may be provided once or multiple times in the course of culturing the cells of the subject invention. For example, the agent(s) may be provided to the subject cells one or more times and the cells allowed to incubate with the agents for some amount of time following each contacting event, e.g. 16-24 hours, after which time the media is replaced with fresh media and the cells are cultured further.

In addition to the one or more reprogramming factors, the reprogramming system may include other reagents. For example, the reprogramming system may include one or more agents known in the art to promote cell reprogramming. Examples of agents known in the art to promote cell reprogramming include GSK-3 inhibitors (e.g. CHIR99021 and the like (see, e.g., Li, W. et al. (2009) Stem Cells, Epub Oct. 16 2009)); histone deacetylase (HDAC) inhibitors (e.g., those described in US20090191159, the disclosure of which is incorporated herein by reference); histone methyltransferase inhibitors (e.g. G9a histone methyltransferase inhibitors, e.g. BIX-01294, and the like (see, e.g. Shi, Y et al. (2008) Cell Stem Cells 3(5):568-574)); agonists of the dihydropyridine receptor (e.g. BayK8644, and the like (see, e.g., Shi, Y et al. (2008) Cell Stem Cell 3(5):568-574)); and inhibitors of TGF signaling (e.g. RepSox and the like (see, e.g. Ichida, J K. et al. (2009) Cell Stem Cell 5(5):491-503)). Examples of agents known in the art to promote cell reprogramming also include agents that reduce the amount of methylated DNA in a cell, for example by suppressing DNA methylation activity in the cell or promoting DNA demethylation activity in a cell. Examples of agents that suppress DNA methylation activity include, e.g., agents that inhibit DNA methyltransferases (DNMTs), e.g. 5-aza-cytidine, 5-aza-2'-deoxycytidine, MG98, S-adenosyl-homocysteine (SAH) or an analogue thereof (e.g. periodate-oxidized adenosine or 3-deazaadenosine), DNA-based inhibitors such as those described in Bigey, P. et al (1999) J. Biol. Chem. 274:459-44606, antisense nucleotides such as those described in Ramchandani, S et al, (1997) Proc. Natl. Acad. Sci. USA 94: 684-689 and in Fournel, M et al, (1999) J. Biol. Chem. 274:24250-24256, or any other DNMT inhibitor known in the art. Examples of agents that promote DNA demethylation activity include, e.g., cytidine deaminases, e.g. AID/APOBEC agents (Bhutani, N et al. (2009) Nature. December 21. [Epub ahead of print]; Rai, K. et al. (2008) Cell 135:1201-1212), agents that promote G:T mismatch-specific repair activity, e.g. Methyl binding domain proteiTr1 cells (e.g. Mbp4) and thymine-DNA glycosylase (TDG) protein (Rai, K. et al. (2008) Cell 135:1201-1212), agents that promote growth arrest and DNA-damage-inducible 45 (GADD45) activity protein (Rai, K. et al. (2008) Cell 135:1201-1212), and the like.

Other reagents of interest for optional inclusion in the reprogramming system are agents known in the art to promote the survival and differentiation of stem cells into T cells and/or progenitors or precursors into T cells. Other reagents of interest for optional inclusion in the reprogramming system are agents that inhibit proliferation, e.g. AraC.

Reagents in the reprogramming system may be provided in any culture media known in the art to promote cell survival, e.g. DMEM, Iscoves, Neurobasal media, etc. In some cases, the media will be DMEM. In some cases, with media will be N3. Media may be supplemented with agents that inhibit the growth of bacterial or yeast, e.g. penicillin/streptomycin, a fungicide, etc., with agents that promote health, e.g. glutamate, and other agents typically provided to culture media as are known in the art of tissue culture.

Non-reprogramming factor reagents of the reprogramming system, e.g. agents that promote demethylation, agents that promote the survival and/or differentiation of T cells or subtypes of T cells, agents that inhibit proliferation, and the like, may be provided to the cells prior to providing the reprogramming factors. Alternatively, they may be provided concurrently with providing the reprogramming factors. Alternatively, they may be provided subsequently to providing the reprogramming factors.

The reprogramming system is provided to non-Tr1 target cells so as to reprogram, i.e. convert, those cells into induced Tr1 cells. Non Tr1 target cells include T cells, e.g. mixed CD4+ cell populations, thymocytes, naïve CD4+ cells, CD8+ cells, T progenitor cells, lymphoid progenitor cells, hematopoietic stem cells, pluripotent stem cells, and the like.

In some embodiments, the target cells are contacted in vitro with the reprogramming system comprising reprogramming factor(s). The subject cells may be from any mammal, including humans, primates, domestic and farm animals, and zoo, laboratory or pet animals, such as dogs, cats, cattle, horses, sheep, pigs, goats, rabbits, rats, mice etc. They may be established cell lines or they may be primary cells, where "primary cells", "primary cell lines", and "primary cultures" are used interchangeably herein to refer to cells and cells cultures that have been derived from a subject and allowed to grow in vitro for a limited number of passages.

The subject cells may be isolated from fresh or frozen cells, which may be from a neonate, a juvenile or an adult, and from tissues including skin, muscle, bone marrow, peripheral blood, umbilical cord blood, spleen, liver, pancreas, lung, intestine, stomach, adipose, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−190° C.) indefinitely. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Cells contacted in vitro with the reprogramming system of reagents, i.e. the one or more reprogramming factors and optionally the one or more other agents that promote reprogramming and promote the growth and/or differentiation of T cells, and the like, may be incubated in the presence of the reagent(s) for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

After contacting the target cells with the reprogramming system, the contacted cells may be cultured so as to promote the survival and differentiation of T cells. Methods and reagents for culturing cells to promote the growth of T cells or particular subtypes of T cells and for isolating T cells or particular subtypes of T cells are well known in the art, any of which may be used in the present invention to grow and isolate the induced Tr1 cells. For example, the target cells (either pre- or post-contacting with the reprogramming factors) may be plated on Matrigel or other substrate as known in the art. The cells may be cultured in media such as N3, supplemented with factors. Alternatively, the contacted cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with lymphocyte survival and differentiation.

The effective amount of a reprogramming system that may used to contact the target cells is an amount that induces at least 0.01% of the cells of the culture to increase expression of one or more phenotypic markers of Tr1 cells, including without limitation over-expression of IL-10. An effective amount is the amount that induces an increase in expression of these genes that is about 1.5-fold or more, e.g. 1.5 fold, 2 fold, 3 fold, 4 fold, about 6 fold, about 10 fold greater than the level of expression observed in the absence of the reprogramming system. The level of gene expression can be readily determined by any of a number of well-known methods in the art, e.g. by measuring RNA levels, e.g. by RT-PCR, quantitative RT-PCR, Northern blot, etc., and by measuring protein levels, e.g. Western blot, ELISA, fluorescence activated cell sorting, etc.

iTr1 cells produced by the above in vitro methods may be used in cell replacement or cell transplantation therapy to treat diseases. Specifically, iTr1 cells may be transferred to subjects suffering from a wide range of diseases or disorders with an immune dysfunction, i.e. with requiring immune suppression such as autoimmune diseases, graft v. host disease, graft rejection, and the like. The therapy may be directed at treating the cause of the disease; or alternatively, the therapy may be to treat the effects of the disease or condition.

The iTr1 cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject.

In some cases, the iTr1 cells are purified or isolated from the rest of the cell culture prior to transferring to the subject. In other words, one or more steps may be executed to enrich for the iTr1 cells or a subpopulation of iTr1 cells. In some cases, one or more antibodies specific for a marker of cells of the Tr1 lineage is incubated with the cell population and those bound cells are isolated. In other cases, the iTr1 cells or a sub-population of the iTr1 cells express a marker that is a reporter gene, e.g. EGFP, dsRED, lacz, and the like, that is under the control of a T cell-specific promoter.

By a marker it is meant that, in cultures comprising target cells that have been reprogrammed to become iTr1 cells, the marker is expressed only by the cells of the culture that will develop, are developing, and/or have developed into T cells. It will be understood by those of skill in the art that the stated expression levels reflect detectable amounts of the marker protein on or in the cell. A cell that is negative for staining (the level of binding of a marker-specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

Cells of interest, i.e. cells expressing the marker of choice, may be enriched for, that is, separated from the rest of the cell population, by a number of methods that are well known in the art. For example, flow cytometry, e.g. fluorescence activated cell sorting (FACS), may be used to separate the cell population based on the intrinsic fluorescence of the marker, or the binding of the marker to a specific fluorescent reagent, e.g. a fluorophor-conjugated antibody, as well as other parameters such as cell size and light scatter. In other words, selection of the cells may be effected by flow cytometry Although the absolute level of staining may differ with a particular fluorochrome and reagent preparation, the data can be normalized to a control. To normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but are not as intense as the most brightly staining cells normally found in the population. An alternative control may utilize a substrate having a defined density of marker on its surface, for example a fabricated bead or cell line, which provides the positive control for intensity.

Other methods of separation, i.e. methods by which selection of cells may be effected, based upon markers include, for example, magnetic activated cell sorting (MACS), immunopanning, and laser capture microdissection.

Enrichment of the iTr1 population or a subpopulation of iTr1 cells may be performed about 3 days or more after contacting the somatic cells with the reprogramming factors of the reprogramming system, e.g. 3 days, 4 days, 5 days, 6 days, 7 days, 10 days, 14 days, or 21 days after contacting the somatic cells with the reprogramming factors. Populations that are enriched by selecting for the expression of one or more markers will usually have at least about 80% cells of the selected phenotype, more usually at least 90% cells and may be 95% of the cells, or more, of the selected phenotype.

In some cases, genes may be introduced into the target cells or the cells derived therefrom, i.e. iTr1 cells, prior to transferring to a subject for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

To prove that one has genetically modified the somatic cells or the cells derived therefrom, i.e. iTr1 cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to T cell lineages while maintaining the ability to express the introduced DNA. Various tests in vitro and in vivo may be employed to ensure that the T cell phenotype of the derived cells has been maintained.

In some approaches, the reprogrammed cells, i.e. iTr1 cells, may be transplanted directly to an injured site to treat an immunological condition.

The iTr1 cells may be administered in any physiologically acceptable medium. They may be provided prior to differentiation, i.e. they may be provided in an undifferentiated state and allowed to differentiate in vivo, or they may be allowed to differentiate for a period of time ex vivo and provided following differentiation. They may be provided alone or with a suitable substrate or matrix, e.g. to support their growth and/or organization in the tissue to which they are being transplanted. Usually, at least $1 \times 10^5$ cells will be administered, preferably $1 \times 10^6$ or more. The cells may be introduced to the subject via any of the following routes: parenteral, intravenous, intracranial, intraspinal, intraocular, or into spinal fluid. The cells may be introduced by injection, catheter, or the like.

The number of administrations of treatment to a subject may vary. Introducing the iTr1 cells into the subject may be a one-time event; but in certain situations, such treatment may elicit improvement for a limited period of time and require an on-going series of repeated treatments. In other situations, multiple administrations of the iTr1 cells may be required before an effect is observed. The exact protocols depend upon the disease or condition, the stage of the disease and parameters of the individual subject being treated.

Additionally or alternatively, iTr1 cells produced by the above in vitro methods may be used as a basic research or drug discovery tool, for example to evaluate the phenotype of a genetic disease, e.g. to better understand the etiology of the disease, to identify target cells for therapeutic treatment, to identify candidate agents with disease-modifying activity, i.e. an activity in modulating the survival or function of T cells in a subject suffering from a disease or disorder, e.g. to identify an agent that will be efficacious in treating the subject. For example, a candidate agent may be added to a cell culture comprising iTr1 cells derived from the subject's cells, and the effect of the candidate agent assessed by monitoring output parameters such as iTr1 survival, functional abilities, and the like, by methods described herein and in the art.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some iTr1 cellstances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Cell Compositions

In some embodiments, an engineered cell is provided, in which the cell has been modified to induce a Tr1 phenotype. In some embodiments, the cell is genetically modified in an ex vivo procedure, prior to transfer into a subject. The engineered cell can be provided in a unit dose for therapy, and can be allogeneic, autologous, etc. with respect to an intended recipient. Methods may include a step of obtaining desired cells, e.g., T cells, hematopoietic stem cells, etc., which may be isolated from a biological sample, or may be derived in vitro from a source of progenitor cells, e.g. iPSC. The cells are transduced or transfected with a vector comprising a sequence encoding the reprogramming factors, which step may be performed in any suitable culture medium. For example, cells may be collected from a patient, modified ex vivo to express a Tr1 reprogramming factors, and reintroduced into the subject. The cells collected from the subject may be collected from any convenient and appropriate source, including e.g., peripheral blood (e.g., the subject's peripheral blood), a biopsy (e.g., a biopsy from the subject), and the like.

Where the use of autologous cells is not desirable, e.g. where a patient has insufficient T cells for modification, where there is insufficient time to expand autologous cells, etc., allogeneic cells may be used, e.g. T cells or stem cells from a healthy donor. As discussed herein, such allogeneic cells can be genetically modified to reduce GVHD, to reduce host versus graft responses, etc.

Engineered cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bolus or slow drip), intraarterial, intraperitoneal, intrathecal or subcutaneous administration.

In Vivo Methods of Conversion, and Uses for Cells Converted In Vivo

In some embodiments, a target cell is contacted in vivo with the reprogramming system comprising reprogramming factor(s), e.g. in a subject in need of therapy. Cells in vivo may be contacted with a system suitable for pharmaceutical use, i.e. a reprogramming pharmaceutical composition, by any of a number of well-known methods in the art for the administration of polypeptides and nucleic acids to a subject. The reprogramming pharmaceutical composition can be incorporated into a variety of formulations. More particularly, the reprogramming pharmaceutical composition can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the reprogramming pharmaceutical composition can be achieved in various ways, including oral, buccal, rectal, parenteral, intraperitoneal, intradermal, transdermal, intracheal, etc., administration. The reprogramming pharmaceutical composition may be systemic after administration or may be localized by the use of regional administration, intramural administration, or use of an implant that acts to retain the active dose at the site of implantation. The reprogramming pharmaceutical composition may be formulated for immediate activity or they may be formulated for sustained release.

The calculation of the effective amount or effective dose of the reprogramming pharmaceutical composition to be administered is within the skill of one of ordinary skill in the art, and will be routine to those persons skilled in the art. Needless to say, the final amount to be administered will be dependent upon the route of administration and upon the nature of the disorder or condition that is to be treated.

For inclusion in a medicament, the reprogramming pharmaceutical composition may be obtained from a suitable commercial source. As a general proposition, the total pharmaceutically effective amount of the compound administered parenterally per dose will be in a range that can be measured by a dose response curve.

The reprogramming pharmaceutical composition to be used for therapeutic administration must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The reprogramming pharmaceutical composition ordinarily will be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The pharmaceutical composition comprising the lyophilized reprogramming factor(s) is prepared by reconstituting the lyophilized compound, for example, by using bacteriostatic Water-for-Injection.

A reprogramming system for pharmaceutical use, i.e. a reprogramming pharmaceutical composition, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the reprogramming pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The reprogramming pharmaceutical composition can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For delivery of iTr1 cells, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g. murine, lagomorpha, etc. may be used for experimental investigations.

More particularly, the present invention finds use in the treatment of subjects, such as human patients, in need of therapy. An effective amount of a reprogramming pharmaceutical composition is the amount that will result in an increase the number of iTr1 T cells at the site of disease, and/or will result in measurable reduction in the rate of disease progression in vivo, the control typically being a subject not treated with the reprogramming pharmaceutical composition. An agent is effective in vivo if administration of the agent at about 1 µg/kg to about 100 mg/kg body weight results in inhibition of symptoms within about 1 month to 3 months from the first administration of the pharmaceutical composition. In a specific aspect, body function may be improved relative to the amount of function observed at the start of therapy.

The methods of the present invention also find use in combined therapies, e.g. in with therapies that are already known in the art to provide relief from symptoms associated with the aforementioned diseases, disorders and conditions. The combined use of a reprogramming pharmaceutical composition of the present invention and these other agents may have the advantages that the required dosages for the individual drugs is lower, and the effect of the different drugs complementary.

Screening methods.

The methods described herein also provide a useful system for screening candidate agents for activity in modulating cell conversion into Tr1 cells. In screening assays for biologically active agents, cells, usually cultures of cells, are contacted with a candidate agent of interest in the presence of the cell reprogramming system or an incomplete cell reprogramming system, and the effect of the candidate agent is assessed by monitoring output parameters such as the level of expression of genes specific for the desired cell typeI, as is known in the art, or the ability of the cells that are induced to function like the desired cell type.

For example, agents can be screened for an activity in promoting reprogramming of cells to a Tr1 cell fate. For such a screen, a candidate agent may be added to a cell culture comprising candidate cells and a reprogramming system or an incomplete reprogramming system, where an observed increase in the level of RNA or protein of a Tr1 gene, e.g. a 1.5-fold, a 2-fold, a 3-fold or more increase in the amount of RNA or protein from a Tr1 expressed gene, over that observed in the culture absent the candidate agent would be an indication that the candidate agent was an agent that promotes reprogramming to a Tr1 fate. Reciprocally, an observed decrease in the level of RNA or protein of a Tr1 gene, e.g. a 1.5-fold, a 2-fold, a 3-fold or more decrease in the amount of RNA or protein from a Tr1 expressed gene as compared to that observed in the culture absent the candidate agent would be an indication that the candidate agent was an agent that suppresses reprogramming to a Tr1 fate. Incomplete reprogramming systems, e.g. a reprogramming system lacking one or more factors, or comprising sub-optimal levels of one or more factors, and the like, may be used in place of a complete reprogramming system to increase the sensitivity of the screen.

As discussed above with regard to uses for iTr1 cells produced by in vitro methods in screening candidate agents for those with an activity in modulating the survival or activity of T cells in a subject suffering from a disease or disorder, candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Also as discussed above, compounds, including candidate agents, may be obtained from a wide variety of sources including libraries of synthetic or natural compounds. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Also as discussed above, candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc. As discussed above, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the chosen parameters. For example, a convention method of measuring the presence or amount of a selected marker is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteiTr1 cells but also specific conformations, cleavage products, or site modifications like phosphorylation. Individual peptides and proteiTr1 cells can be engineered to autofluoresce, e.g. by expressing them as green fluorescent protein chimeras iTr1 cellside cells (for a review see Jones et al. (1999) Trends Biotechnol. 17(12): 477-81).

Kits may be provided, where the kit will comprise one or more factors to promote the conversion of cells into Tr1 cells. A combination of interest may include one or more reprogramming polypeptides or vectors comprising nucleic acids encoding those polypeptides. Kits may further include cells or reagents suitable for isolating and culturing cells in preparation for conversion; reagents suitable for culturing T cells; and reagents useful for determining the expression of Tr1 genes in the contacted cells. Kits may also include tubes, buffers, etc., and instructions for use.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Provided is a demonstration of isolation and whole transcriptome analyses via RNA sequencing on Tr1 cells from healthy human peripheral blood mononuclear cells (PBMC). We have analyzed these data to identify transcription factors that are significantly preferentially expressed by Tr1 cells and selected seven transcription factors for further analysis.

To screen these candidate transcription factors, we overexpressed them, in a tetracycline dependent TetON system, alone or in combination in primary total $CD4^+$ T cells isolated from healthy PBMCs. After expansion, these transgenic $CD4^+$ T cells were stimulated with antibodies against CD3 and CD28 to measure IL-10 secretion via Enzyme-Linked Immunosorbent Assay (ELISA). After screening these seven transcription factors, we have identified three transcription factors: BHLHE40, ID2, and AHR, that when overexpressed, induced functional changes in the CD4+ T cells including upregulation of IL-10, reduced proliferation in response to stimulation, and expression of inhibitory molecules. BHLHE40 alone and ID2 and AHR in combination, give rise to IL-10 secreting Tr1-like cells.

The methods find use in developing: a protocol generating IL-10 producing human Tr1 cells by overexpressing transcription factors in human CD4+ T cells. A method to specifically identify, quantify, and track Tr1 cells in vivo in healthy individuals and patients. Screening methods to identify small molecules that activate these transcription factors or block known inhibitors of these transcription factors to differentiate Tr1 cells in vitro and in vivo. Transgenic iPSC line containing a genetic construct with the specified transcription factors sufficient for producing IL-10 secreting human CD4+ T cells operably linked to a promoter active in the cells. A protocol that differentiates human IL-10 producing CD4+ T cells, starting from the transgenic iPSC described. Establishing a GMP compatible feeder free system to differentiate and expand IL-10 producing CD4+ human T cells.

Two Tr1 cell-based therapy clinical trials, ALT TEN and CATS1, have been completed and one is currently on-going (ClinicalTrial.gov identifier NCT3198234). ALT TEN was a proof of concept study that utilized host alloantigen specific IL-10-anergized donor T cells in order to reduce graft versus host disease after haploidentical hematopoietic cell transplant in hematologic malignancies (Bacchetta et al. 2014). Of the 5 patients that had immune reconstitution, 4 patients all had high-risk/advanced stage hematologic malignancies, received a dose of $10^5$ CD3+ cells/kg, and had low GvHD. In the 7.2 year median follow-up, the 4 described patients are alive, in complete disease remission, and are immunosuppression independent. The 1 patient who received a higher dose of $3 \times 10^5$ CD3+ cells/kg had immune reconstitution and grade III acute GvHD. Therefore, the lower cell dose of $10^5$ CD3+ cells/kg was shown to be safe and feasible. The ongoing clinical trial, NCT3198234, utilizes similar biological principles as those in ALT TEN to generate the cell product, but with notable manufacturing and trial design differences; the cell product in this trial is referred to as "T-allo10". The following improvements to be described are applicable to both clinical trials mentioned above. The process of generating this Tr1 cell-based product requires precise and synchronized coordination of collecting and differentiating donor CD4+ T cells and recipient monocytes. Because this system is a mixed lymphocyte reaction, both differentiated monocytes and CD4+ T cells must be carefully characterized and compatible for the entire processes to work, thus leaving more production variables and personalization of processing. Our protocol only requires a single collection of blood to then isolate CD4+ T cells as starting material.

The CATS1 completed clinical trial utilized a protocol described in Brun et al. 2009 Int Immunopharmacol, in which OVA-specific Tr1 cell clones are utilized to treat refractory Chron's disease (Desreumaux et al. 2012). The production method utilizes a feeder cell layer of transgenic Drosophila origin (Schneider cells) that support the expansion of Tr1 cells. They report that after 12-15 weeks, they yield more than 5 billion monoclonal Tr1 cells. While this process is durable (they report success in more than 90% of 50 tested healthy donors), it is tedious; the process requires single cell cloning through a limiting dilution method, screening of many potential clones, and weekly stimulation with feeder cells over many weeks. Additionally, the clinical trial reported that in the group receiving the highest dose of $10^9$ cells/kg, there was an increase in preexisting serum IgG antibodies agaiTr1 cellst Drosophila antigen due to impurities in the product.

Besides the aforementioned clinical trials, another existing method to generate in vitro induced Tr1 cells is by constitutively expressing IL-10 in CD4+ T cells ($CD4^{LV-10}$; Andolfi et al. 2012). The IL-10 transgene is integrated by lentivirus and its expression is controlled under the phosphoglycerate kinase promoter. $CD4^{LV-10}$ cells possess many of the Tr1 functional hallmarks. However, since the IL-10 promoter is constitutively expressed, there is no cell intrinsic regulation of IL-10. By overexpressing the upstream transcription factor(s), the Tr1 phenotype, which includes IL-10 expression can be self-regulated.

Variations of the method include overexpressing BHLHE40 or AHR with ID2 with various promoters, including constitutive promoters such as PGK, EF1a. Changing the expansion protocol to use a non-cell based artificial antigen presenting method such as antibody coated beads or nanoparticles. Generating antigen specific IL-10 producing human CD4+ T cells iTr1 cellstead of using polyclonal CD4+ T cells. Differentiating IL-10 producing human CD4+ T cells by starting with a subset of CD4+ T cells, including but not limited to naïve CD4+ T cells, effector memory CD4+ T cells, and Th1 cells.

BHLHE40 has been largely overlooked in human Tr1 cells because it has been shown in the mice to downregulate IL-10. However, our data indicate that the function of BHLHE40 is divergent between human and mouse. We have performed RNA sequencing on three cell populations: ex vivo sorted Tr1, $CD4^{LV-IL10}$, and T-allo10; the penultimate and ultimate induced Tr1 populations were generated by two distinct methods described in Andolfi et al. 2012 and clinical trial NCT03198234 respectively. We show that BHLHE40 is one of the transcription factors that is differentially upregulated in all the Tr1 and induced Tr1 populations. Furthermore, in our system where we overexpress BHLHE40 in primary human CD4+ T cells, we find that IL-10 is iTr1 cellstead upregulated.

AHR requires ligand binding in order to translocate to the nucleus and bind to DNA to initiate transcription. Ligand activated AHR has been characterized in human and mouse T cells to different extents. In the human, three hypotheses are 1) ligand activated AHR and IL-27 differentiates Tr1 cells; 2) ligand activated AHR in combination with TGF-B differentiates FOXP3+ induced Tregs; 3) limited ligands that activate AHR in coordination with transcription factor cMAF differentiates Th17 cells. A major caveat in these studies is that the Tr1 differentiation method utilizes IL-27, which has not been well established in human cells as compared to mouse cells. (Apetoh et al. 2010 Nature Immunology). Even though many hypothesize the important of AHR in Tr1 differentiation and function, the exact mechanism is still unclear. We do know though that in our previously published study, studies published by other groups, and our new RNA sequencing data that AHR is expressed highly on a transcriptional level but not differentially expressed compared to the controls.

Therefore, AHR may act synergistically with another transcription factor in order to push the cells to adopt a Tr1 fate. We chose to co-express AHR with ID2. ID2 can heterodimerize to a subset of transcription factors that contain the beta-helix-loop-helix motif to inhibit DNA binding. In our bulk ATAC-sequencing analyses of Tallo10/Tallo cells, the transcriptional start site of ID2 showed increase accessibility. This is further supported by our RNAseq data of Tallo10 and Tallo which showed that Tallo10 upregulate ID2 as compared to Tallo. Additionally, ID2 can competitively bind transcription factor 3 (TCF3; Langlands et al. 1997), which is a known repressor of AHR transcriptional activation in IL-22 producing cells (Gou et al. 2015). Co-expression of AHR and ID2 may lead to an increase in AHR-mediated IL-10 transcription.

Tr1 cells have been described in many disease settings in which the tolerogenic axis is disrupted including, but not limited to autoimmune diseases (e.g. type 1 diabetes, multiple sclerosis), allergy (allergic asthmatic, bee venom), transplantation (graft versus host disease), and tumor (metastatic melanoma and liver tumors). Now that we have identified transcription factors that can polarize CD4+ T cells to secret IL-10, we can utilize these transcription factors as a potential new target for generating in vivo and in vitro Tr1 cells as a cell-based therapy. Unlike many of the clinical trials that utilize thymic derived regulatory T cells, Tr1 cells can be generated in an antigen specific manner appropriate for the disease setting to generate potentially more efficacious cell therapies.

We focus on identifying and characterizing human Tr1-specific protein markers using ex vivo, T-allo10 and LV-10 Tr1. We also ask whether there is a functional relationship between the candidate biomarkers and key Tr1 cytokine, IL-10.

While master TFs have been identified for many other human T cell subsets: FOXP3 for Tregs, T-bet for Th1 cells, GATA3 for Th2 cells and ROR-γt for Th17 cells, no master TFs have been confirmed for human Tr1 cells. In murine studies, BATF and IRF1 have been suggested as defining TFs for early Tr1 lineage development. In addition, several groups have identified mouse TFs with roles in induction of the key Tr1 cytokine, IL-10, in CD4+ T cells. These studies suggest a defining role for IL-27 signaling in promoting numerous transcriptional pathways leading to transactivation of 1110 expression. These include EGR-2, which activates expression of Blimp-1 (encoded by Prdm1), and c-Maf, through interaction with AHR. Additional mouse studies have proposed a role for the transcription factors Eomes (through T-bet) and Ror-α in transactivating the 1110 gene in CD4+ Tcells.

But despite significant progress in dissecting these transcriptional pathways in mice, murine Tr1 master regulators have not been verified in human cells. We investigate the functional role of human TFs identified as upregulated in our human ex vivo, T-allo10 and LV-10 Tr1 datasets, and include analysis of their relationship to IL-10 expression.

Lineage-specifying transcription factors that impact cell function and phenotype and have been established for several other T cell subsets. While several studies have identified murine Tr1 TFs, and pathways leading to activation of murine IL-10, none have looked in human Tr1. Out of 13 TFs previously associated with murine Tr1 or IL-10 regulation in mice, we found 9 significantly different in our dataset, but only BHLHE40 was upregulated in more than 1 Tr1 subtype. We began our search for human Tr1 TFs by functionally validating the selected TFs BHLHE40, BLIMP-1 (PRDM1), AHR and ID2 by overexpression or CRISPR/Cas9 knock-out in CD4+ T cells. We show that one or more TF impact Tr1 suppressive activity, phenotype and/or IL-10 expression.

We have tested the impact of overexpression of 3 candidate TFs BHLHE40 and AHR plus ID2 on IL-10 production. BHLHE40 is an IL10 gene repressor in mice, but we found it upregulated in human T-allo10 and ex vivo Tr1. AHR has been implicated in activation of IL-10 production in murine Tr1 cells and was upregulated in ex vivo Tr1 in our transcriptome analysis. We co-expressed AHR with ID2 because ID2 can competitively bind transcription factor 3 (TCF3), which is a repressor of AHR transcriptional activation. We hypothesized that overexpression of ID2 with AHR will lead to an increase in AHR-mediated IL-10 transcription. Consistent with our hypothesis, bulk ATAC-seq analysis of Tallo10 and control cells showed increased accessibility upstream of ID2 in T-allo10, and ID2 gene was significantly upregulated in T-allo10 Tr1.

We used lentiviral delivery of an all-in-one TetON inducible system to express the TFs upon addition of doxycycline. We determined the optimal dox dose (1 μg/mL) using 293T cell line then delivered GFP into CD4+ T cells to confirm that transgene expression is maintained during stimulation. Finally, we overexpressed BHLHE40, or AHR+ID2 in CD4+ T cells. The transduced CD4+ T cells were expanded over feeder cells, with exogenous IL-10 added for the first 12 days. After 2 feeder cycles, CD4+ T cells were stimulated for 6 h with PMA and ionomycin in the presence of protein transport inhibitors to detect intracellular IL-10 by flow cytometry, or for 48 h with anti-CD3/CD28 to detect secreted IL-10 by ELISA. In two donors, BHLHE40 overexpression or AHR+ID2 (but not either alone) led to increased intracellular or secreted (right) IL-10. These data show that BHLHE40 and AHR+ID2 impact IL-10 regulation.

We will also evaluate if over-expression of candidate TFs and signaling proteins confers Tr1 cytokine phenotype and suppressive function. We will repeat our experiments with BHLHE40 and AHR/ID2, and we will test TF PRDM1 identified in our analysis of the bulk RNA-seq and ATAC-seq data. We will perform these experiments in 3 donors with two rounds of expansion to assay the cells when they have a stable phenotype. We will assay Tr1 signature cytokines (IL-10, IR*, IL-4, IL-17), expression of co-inhibitory molecules that may contribute to Tr1 suppressive function (e.g. LAG3, PD-1, CTLA-4, TIM-3, TIGIT, OX40, ICOS), and the ability to suppress the proliferation of $T_{EFF}$ in vitro. Candidate genes are overexpressed using the lentiviral TetON system. Engineered CD4+ T cells and their mock-treated control cells are expanded over feeder cells with or without exogenous IL-10, to mimic the LV-10/LV-GFP production protocol. After expansion, we will test the engineered CD4+ T cells for: i) Tr1 cytokine secretion profile (IL-10$^{++}$/IFNγ$^+$/IL-4$^{low}$/IL17$^{low}$) by intracellular cytokine staining and ELISA after 6 h stimulation with PMA/ionomycin or 48 h stimulation with anti-CD3/CD28, respectively; ii) capacity to suppress the proliferation of $T_{EFF}$; and iii) expression of current and candidate Tr1 biomarkers.

Example 2

Figure 9:
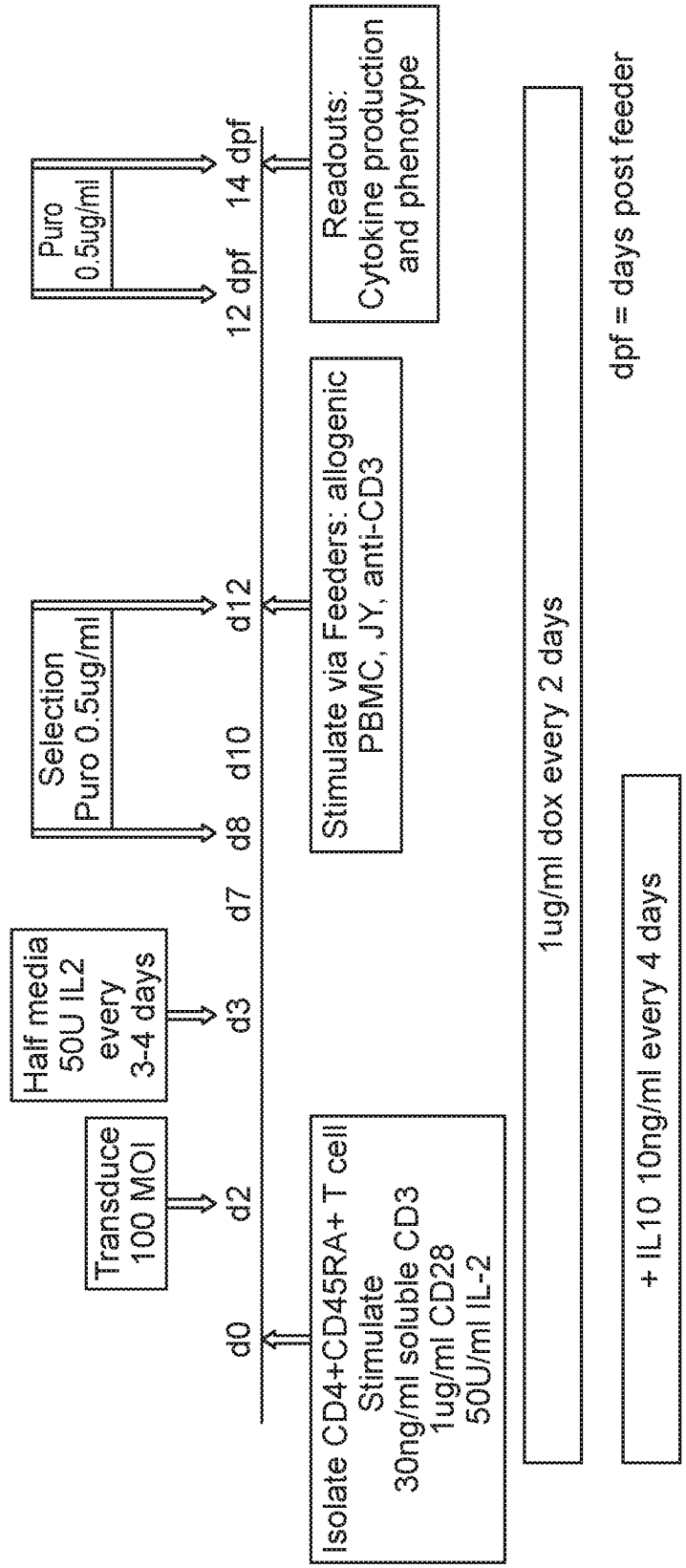
FIG. 9. Method for overexpressing TFs using a dox inducible system in naïve CD4+ T cells.

Method for overexpressing TFs using a dox inducible system in naive CD4+ T cells. The overexpression method was adapted to use naïve CD4+ T cells isolated from umbilical cord blood. The starting cells were exposure to minimal activation using 30 ng/ml soluble CD3, 1 ug/ml CD28, 50 U/ml IL-2 and IL-10 10 ng/ml. Cells are transduced with 100 MOI for 1 day and then maintained in 50 U IL2/ml, which was refreshed every 3-4 days. Dox is refreshed every 2 days to maintain overexpression levels. Transduced cells are selected for by puromycin selection for 4 days. Cells were expanded using an allogenic feeder mixture which consists of X ray irradiated allogenic peripheral blood mononuclear cells with JY cells, and 1 ug/ml soluble anti-CD3. All readouts were performed 14 days after coculturing with the irradiated feeder mixture. Diagram provided in FIG. 9

Figure 10A:
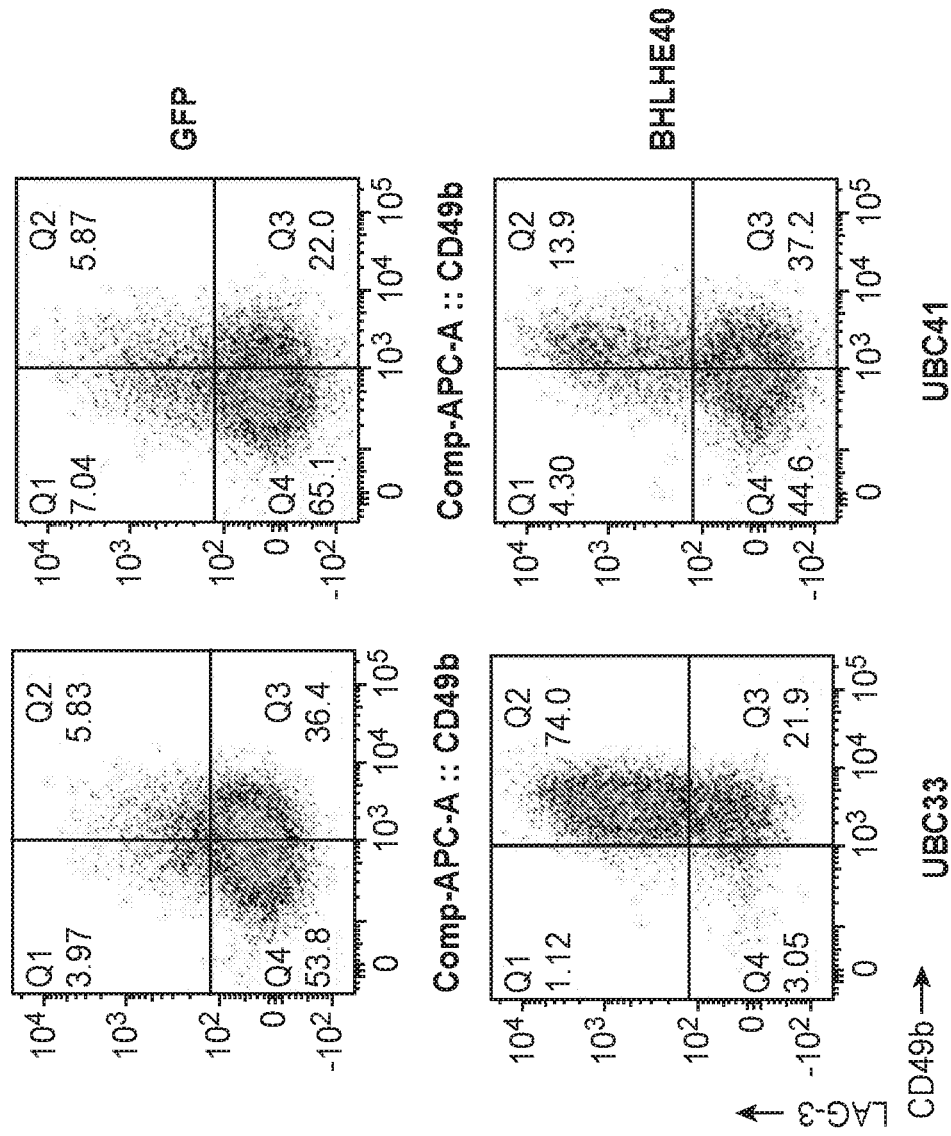
FIG. 10A-C. A. BHLHE40 in both donors has a distinct LAG3+/CD49b+ population. B. HLF overexpression in naïve CD4+ T cells also had an increase in LAG3+/CD49b+. C. BHLHE40 in both donors has a higher LAG3+/CD49b+ population.
Figure 10B:
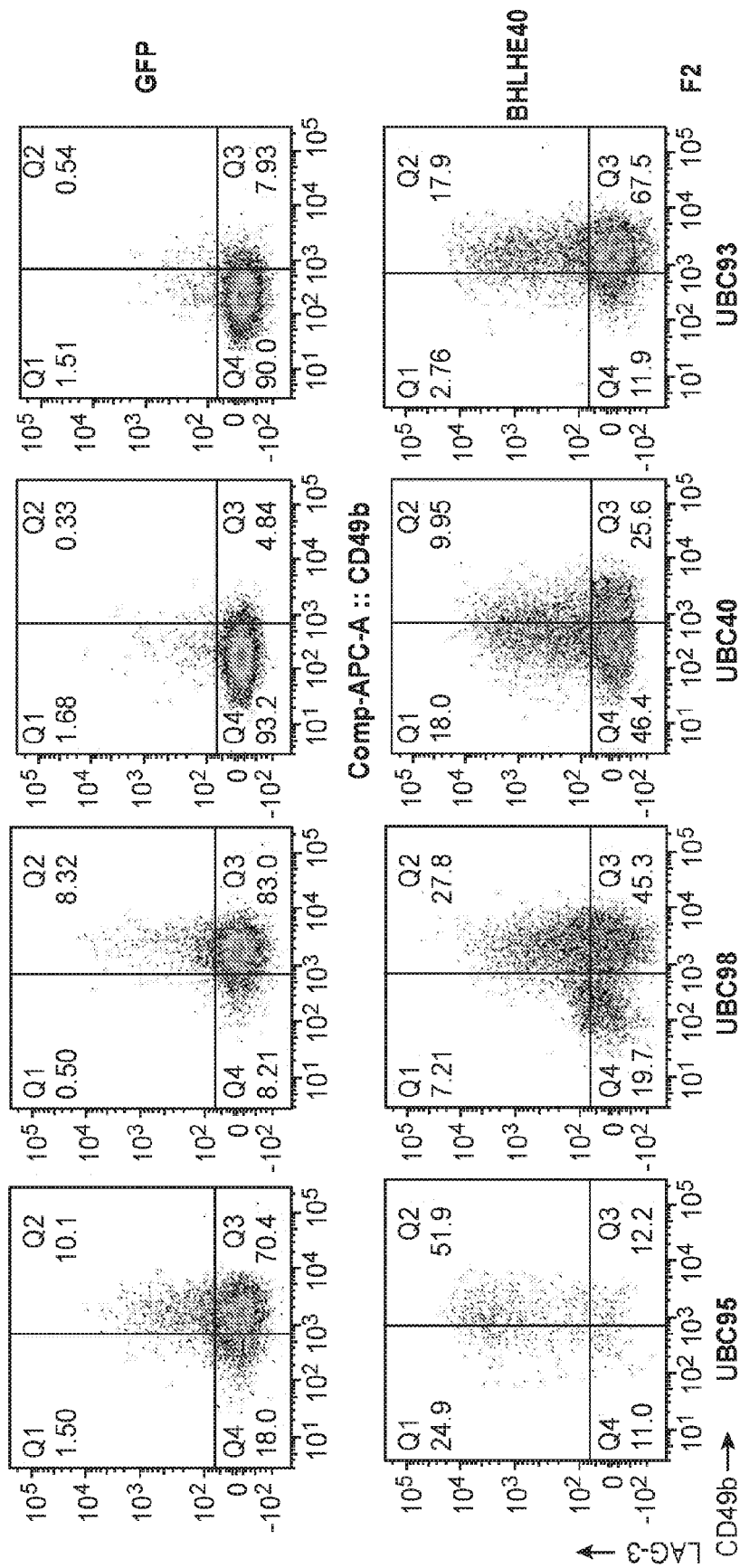
Figure 10C:
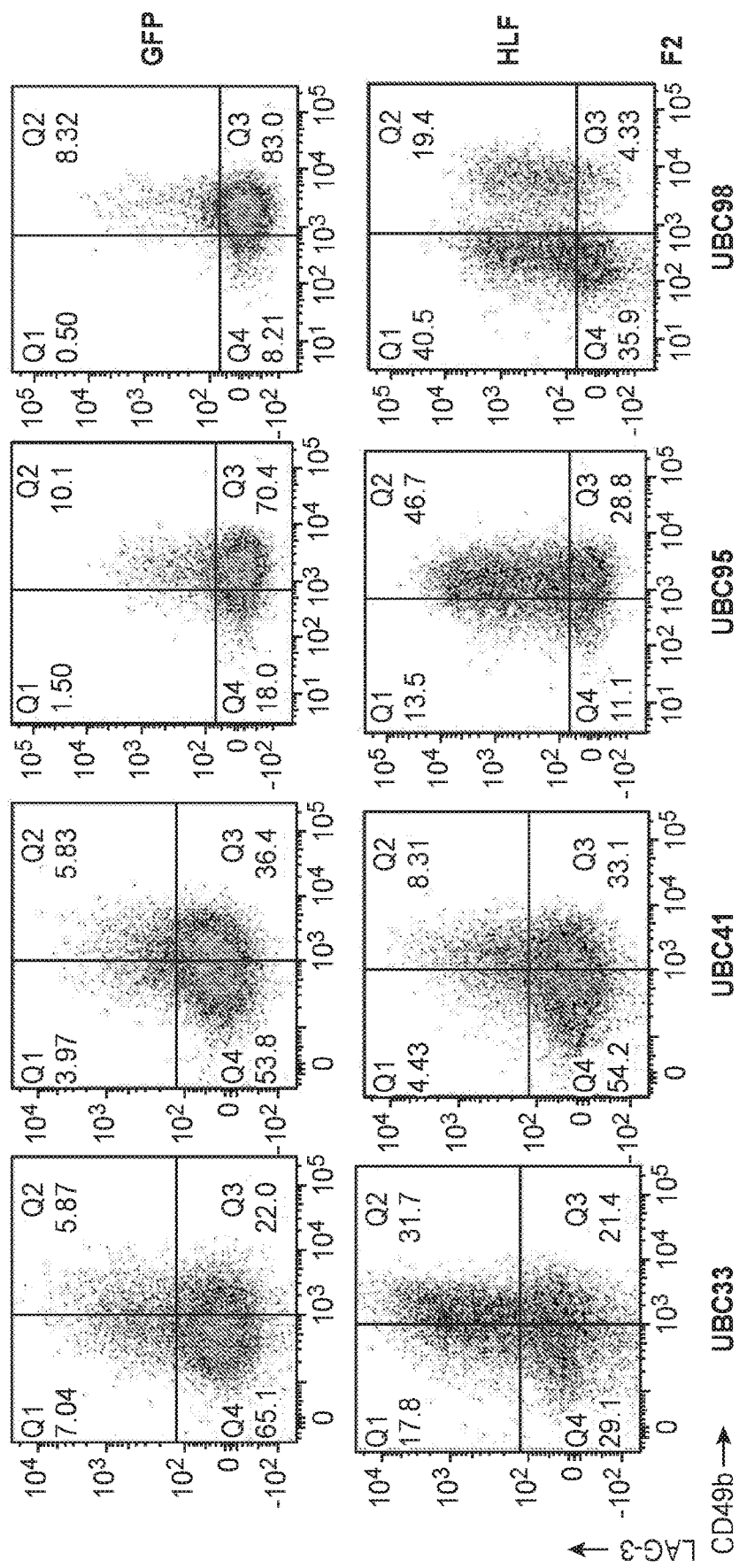

Naïve T cells transformed to overexpress BHLHE40 or HLF showed a distinct LAG3+/CD49b+ population, subgated on CD4+/CD8-/live cells, although more pronounced with BHLHE40 (shown in FIG. 10). Phenotypic surface staining on cells after 2 rounds of expansion on irradiated feeder mixture. Each UBC denotes a different umbilical cord blood donor. Cells were stained with CD8, CD4, viability dye, CD49b, LAG3 at day 14 at the end of the 2$^{nd}$ round of feeder expansion. The control is TetO-GFP in which cells are only expressing GFP upon dox induction, while the experimental condition is expressing either BHLHE40 or HLF, both transcription factors. There is an increase in LAG3+/CD49b+ cells upon induction of either HLF or BHLHE40. Results were read on BD Aria flow cytometer.

Figure 11:
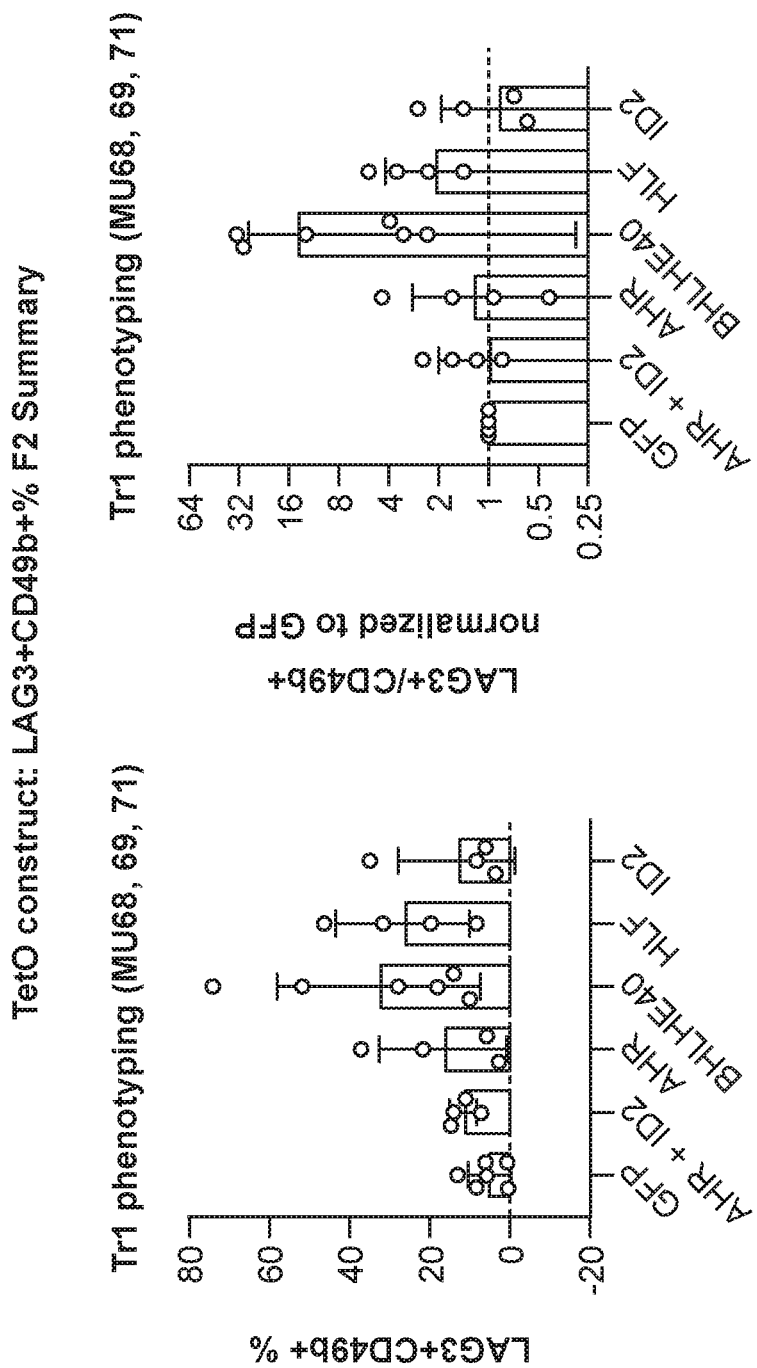
FIG. 11. TetO construct: LAG3+CD49b+% summary.
Figure 12:
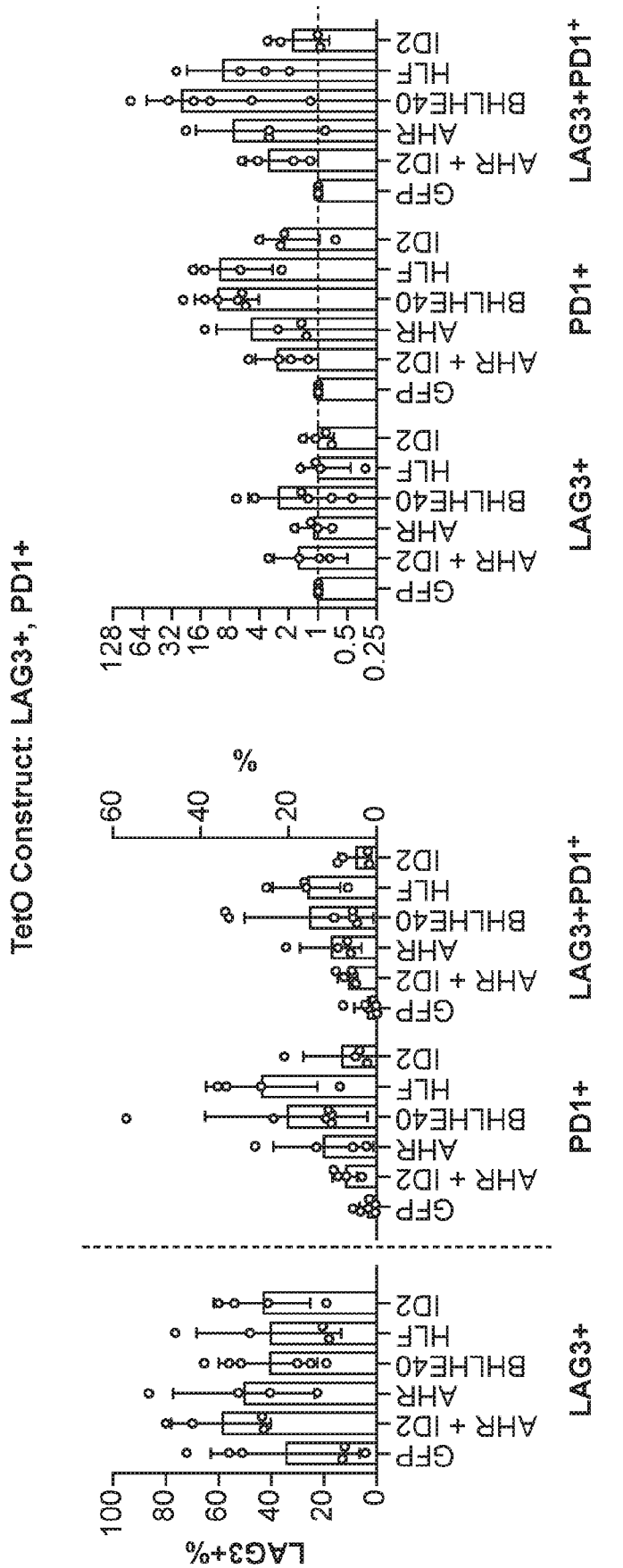
FIG. 12. TetO Construct: LAG3+,PD1+.
Figure 13:
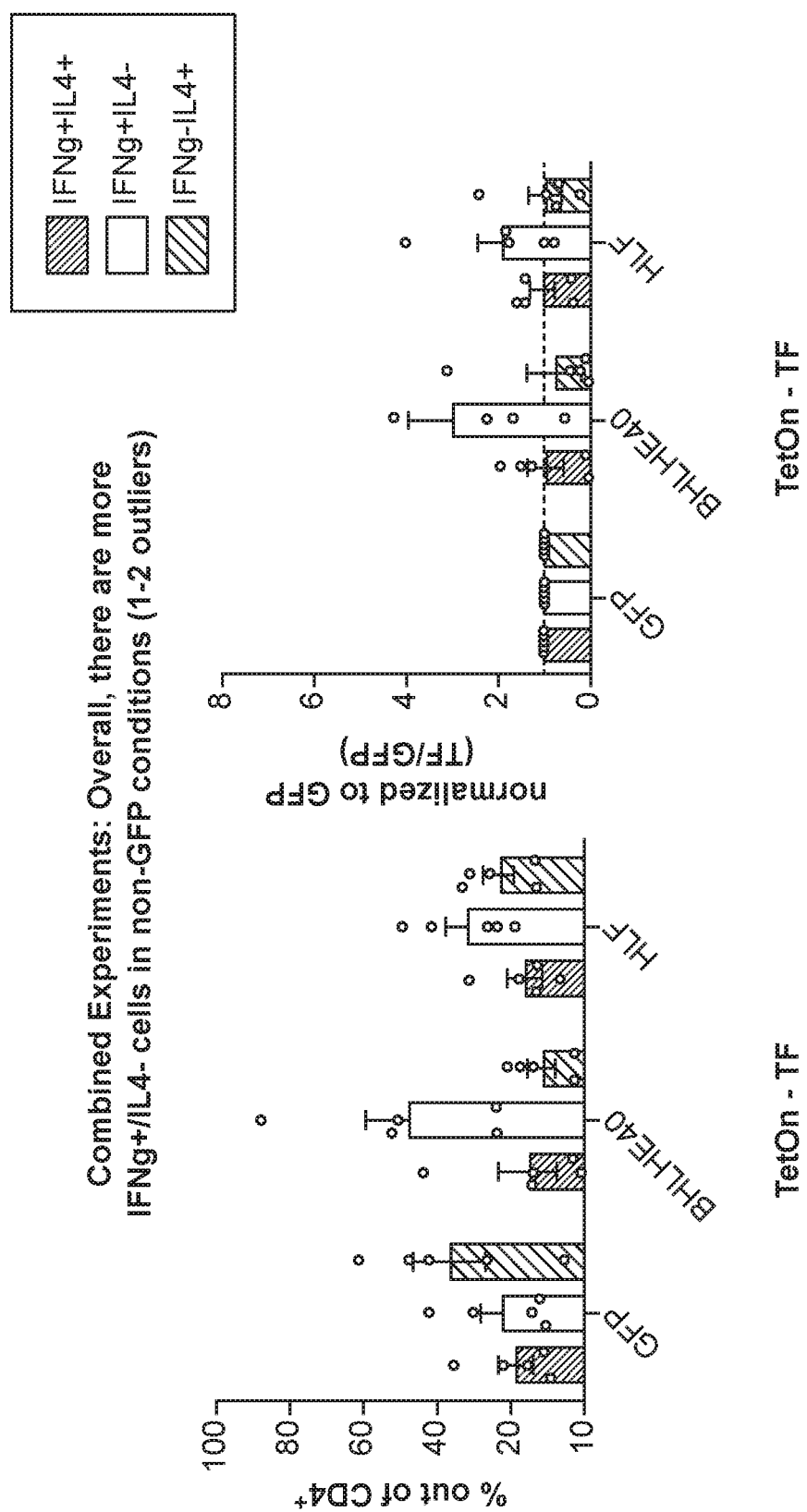
FIG. 13. Summary of combined experiments, showing that overall there are more IFNγ⁺/IL4⁻ cells in non-GFP conditions, i.e. where transcription factors are over-expressed.

Shown in FIGS. 11 and 12 is a summary of the LAG3+ cells expressing PD1 or CD49b. The percentage represents the number of CD49b+/LAG3+/CD4+/live cells upon overexpression of the gene indicated on the x-axis. Each dot represents a different umbilical cord donor. (Right) Normalized LAG3+/CD49b+ are calculated by dividing the LAG3+/CD49b+% in the experimental condition by the LAG3+/CD49b+% in the GFP. In FIG. 12, cells are stained with CD3, CD8, viability dye, PD1+, LAG3+ at day 14 at the end of the $2^{nd}$ round of feeder expansion. Shown is the percentage of LAG3+/CD4+/live cells, PD1+/CD4+/live cells, LAG3+/PD1+/CD4+/live cells. The control is TetO-GFP in which cells are only expressing GFP upon dox induction, while the experimental condition is expressing either BHLHE40 or HLF, both transcription factors. There is an increase in PD1+ and PD1+/LAG3+ cells upon induction of either HLF or BHLHE40. (Right panel) Normalized % are calculated by dividing the % in the experimental condition by the % in the GFP.

Overall, there are more IFNγ/IL4⁻ cells in the populations overexpressing the transcription factors as noted, relative to the control (GFP) conditions. Intracellular cytokine staining on cells after 2 rounds of expansion on irradiated feeder mixture after stimulating with leukocyte activation cocktail per the manufacturer's instructions for 5 hours. Following stimulation, cells were first stained with CD4 and a fixable viability dye and then fixed with 4% paraformaldehyde. Following fixation, cells were permeabilized with BD Fix/Perm wash kit for 15 mins and then stained with monoclonal antibodies: IFNg, IL-4, IL-2, IL-10, IL-17. Shown here are the percentages of cells stained positive for the indicated cytokine. Each colored dot denotes a different umbilical cord blood donor. Results were read on Beckman Coulter Cytoflex flow cytometer. (Right panel) Normalized % are calculated by dividing the % in the experimental condition by the % in the GFP.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of converting human non-Type 1 regulatory (Tr1) cells into induced Tr1 cells (iTr1), the method comprising:
   contacting a population of non-Tr1 with a Tr1 reprogramming system comprising a genetic sequence encoding BHLHE40 protein, for a period of time sufficient to reprogram said non-Tr1 cells to LAG3+/CD49b+T cells,
   wherein a population of iTr1 cells is produced.

2. The method of claim 1 wherein the non-Tr1 cells are T cells.

3. The method of claim 1, wherein the non-Tr1 cells are CD4+T cell.

4. The method of claim 1 wherein the non-Tr1 cells are lymphoid stem or progenitor cells.

5. The method of claim 1 wherein the non-Tr1 cells are pluripotent cells.

6. The method of claim 1, wherein the non-Tr1 cells are isolated from a patient for ex vivo engineering.

7. The method of claim 1, wherein the cells are allogeneic.

8. A method of converting human non-Type 1 regulatory (Tr1) cells into induced Tr1 cells (iTr1), the method comprising:
   contacting a population of non-Tr1 with a Tr1 reprogramming system comprising a sequence encoding protein for a period of time sufficient to reprogram said non-Tr1 cells,
   wherein a population of iTr1 cells is produced.

9. A method of converting human CD4+T cells into induced LAG3+/CD49b+Tr1 cells (iTr1), the method comprising:
   contacting a population of human CD4+T cells ex vivo with a Tr1 reprogramming system comprising a genetic sequence encoding BHLHE40 protein, for a period of time sufficient to reprogram said CD4+T cells to LAG3+/CD49b+iTr1 cells,
   wherein a population of LAG3+/CD49b+iTr1 cells is produced.

10. The method of claim 9, wherein the human CD4+T cells are isolated from a patient for ex vivo engineering.

11. The method of claim 9, wherein the human CD4+T cells are allogeneic.

* * * * *

SEQUENCE LISTING

```
<160> NUMBER OF SEQ ID NOS: 4

<210> SEQ ID NO 1
<211> LENGTH: 412
<212> TYPE: PRT
<213> ORGANISM: Homo sapiens

<400> SEQUENCE: 1

Met Glu Arg Ile Pro Ser Ala Gln Pro Pro Ala Cys Leu Pro Lys
1               5                   10                  15

Ala Pro Gly Leu Glu His Gly Asp Leu Pro Gly Met Tyr Pro Ala His
                20                  25                  30

Met Tyr Gln Val Tyr Lys Ser Arg Arg Gly Ile Lys Arg Ser Glu Asp
            35                  40                  45

Ser Lys Glu Thr Tyr Lys Leu Pro His Arg Leu Ile Glu Lys Lys Arg
        50                  55                  60

Arg Asp Arg Ile Asn Glu Cys Ile Ala Gln Leu Lys Asp Leu Leu Pro
65                  70                  75                  80

Glu His Leu Lys Leu Thr Thr Leu Gly His Leu Glu Lys Ala Val Val
                85                  90                  95

Leu Glu Leu Thr Leu Lys His Val Lys Ala Leu Thr Asn Leu Ile Asp
                100                 105                 110

Gln Gln Gln Gln Lys Ile Ile Ala Leu Gln Ser Gly Leu Gln Ala Gly
            115                 120                 125

Glu Leu Ser Gly Arg Asn Val Glu Thr Gly Gln Glu Met Phe Cys Ser
        130                 135                 140

Gly Phe Gln Thr Cys Ala Arg Glu Val Leu Gln Tyr Leu Ala Lys His
145                 150                 155                 160
```

```
Glu Asn Thr Arg Asp Leu Lys Ser Ser Gln Leu Val Thr His Leu His
                165                 170                 175

Arg Val Val Ser Glu Leu Leu Gln Gly Gly Thr Ser Arg Lys Pro Ser
            180                 185                 190

Asp Pro Ala Pro Lys Val Met Asp Phe Lys Glu Lys Pro Ser Ser Pro
        195                 200                 205

Ala Lys Gly Ser Glu Gly Pro Gly Lys Asn Cys Val Pro Val Ile Gln
210                 215                 220

Arg Thr Phe Ala His Ser Ser Gly Glu Gln Ser Gly Ser Asp Thr Asp
225                 230                 235                 240

Thr Asp Ser Gly Tyr Gly Gly Glu Ser Glu Lys Gly Asp Leu Arg Ser
            245                 250                 255

Glu Gln Pro Cys Phe Lys Ser Asp His Gly Arg Arg Phe Thr Met Gly
        260                 265                 270

Glu Arg Ile Gly Ala Ile Lys Gln Glu Ser Glu Glu Pro Pro Thr Lys
    275                 280                 285

Lys Asn Arg Met Gln Leu Ser Asp Asp Glu Gly His Phe Thr Ser Ser
290                 295                 300

Asp Leu Ile Ser Ser Pro Phe Leu Gly Pro His Pro His Gln Pro Pro
305                 310                 315                 320

Phe Cys Leu Pro Phe Tyr Leu Ile Pro Pro Ser Ala Thr Ala Tyr Leu
            325                 330                 335

Pro Met Leu Glu Lys Cys Trp Tyr Pro Thr Ser Val Pro Val Leu Tyr
        340                 345                 350

Pro Gly Leu Asn Ala Ser Ala Ala Leu Ser Ser Phe Met Asn Pro
    355                 360                 365

Asp Lys Ile Ser Ala Pro Leu Leu Met Pro Gln Arg Leu Pro Ser Pro
370                 375                 380

Leu Pro Ala His Pro Ser Val Asp Ser Ser Val Leu Leu Gln Ala Leu
385                 390                 395                 400

Lys Pro Ile Pro Pro Leu Asn Leu Glu Thr Lys Asp
            405                 410

<210> SEQ ID NO 2
<211> LENGTH: 295
<212> TYPE: PRT
<213> ORGANISM: Homo sapiens

<400> SEQUENCE: 2

Met Glu Lys Met Ser Arg Pro Leu Pro Leu Asn Pro Thr Phe Ile Pro
1               5                   10                  15

Pro Pro Tyr Gly Val Leu Arg Ser Leu Leu Glu Asn Pro Leu Lys Leu
            20                  25                  30

Pro Leu His His Glu Asp Ala Phe Ser Lys Asp Lys Asp Lys Glu Lys
        35                  40                  45

Lys Leu Asp Asp Glu Ser Asn Ser Pro Thr Val Pro Gln Ser Ala Phe
    50                  55                  60

Leu Gly Pro Thr Leu Trp Asp Lys Thr Leu Pro Tyr Asp Gly Asp Thr
65                  70                  75                  80

Phe Gln Leu Glu Tyr Met Asp Leu Glu Glu Phe Leu Ser Glu Asn Gly
                85                  90                  95

Ile Pro Pro Ser Pro Ser Gln His Asp His Ser Pro His Pro Pro Gly
            100                 105                 110

Leu Gln Pro Ala Ser Ser Ala Ala Pro Ser Val Met Asp Leu Ser Ser
```

```
            115                 120                 125

Arg Ala Ser Ala Pro Leu His Pro Gly Ile Pro Ser Pro Asn Cys Met
130                 135                 140

Gln Ser Pro Ile Arg Pro Gly Gln Leu Leu Pro Ala Asn Arg Asn Thr
145                 150                 155                 160

Pro Ser Pro Ile Asp Pro Asp Thr Ile Gln Val Pro Val Gly Tyr Glu
                165                 170                 175

Pro Asp Pro Ala Asp Leu Ala Leu Ser Ser Ile Pro Gly Gln Glu Met
            180                 185                 190

Phe Asp Pro Arg Lys Arg Lys Phe Ser Glu Glu Glu Leu Lys Pro Gln
        195                 200                 205

Pro Met Ile Lys Lys Ala Arg Lys Val Phe Ile Pro Asp Asp Leu Lys
210                 215                 220

Asp Asp Lys Tyr Trp Ala Arg Arg Arg Lys Asn Asn Met Ala Ala Lys
225                 230                 235                 240

Arg Ser Arg Asp Ala Arg Arg Leu Lys Glu Asn Gln Ile Ala Ile Arg
                245                 250                 255

Ala Ser Phe Leu Glu Lys Glu Asn Ser Ala Leu Arg Gln Glu Val Ala
            260                 265                 270

Asp Leu Arg Lys Glu Leu Gly Lys Cys Lys Asn Ile Leu Ala Lys Tyr
        275                 280                 285

Glu Ala Arg His Gly Pro Leu
290                 295

<210> SEQ ID NO 3
<211> LENGTH: 848
<212> TYPE: PRT
<213> ORGANISM: Homo sapiens

<400> SEQUENCE: 3

Met Asn Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
                20                  25                  30

Ser Asn Pro Ser Lys Arg His Arg Asp Arg Leu Asn Thr Glu Leu Asp
            35                  40                  45

Arg Leu Ala Ser Leu Leu Pro Phe Pro Gln Asp Val Ile Asn Lys Leu
        50                  55                  60

Asp Lys Leu Ser Val Leu Arg Leu Ser Val Ser Tyr Leu Arg Ala Lys
65                  70                  75                  80

Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
            100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
            180                 185                 190
```

```
Ala Thr Gly Leu Pro Gln Thr Val Val Cys Tyr Asn Pro Asp Gln Ile
            195                 200                 205

Pro Pro Glu Asn Ser Pro Leu Met Glu Arg Cys Phe Ile Cys Arg Leu
210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
            275                 280                 285

Thr Lys His Lys Leu Asp Phe Thr Pro Ile Gly Cys Asp Ala Lys Gly
        290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
        370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
            405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
        530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Ser Leu Ala Leu Asn
            595                 600                 605

Ser Ser Cys Met Val Gln Glu His Leu His Leu Glu Gln Gln Gln Gln
```

```
                610                 615                 620
His His Gln Lys Gln Val Val Glu Pro Gln Gln Leu Cys Gln
625                 630                 635                 640

Lys Met Lys His Met Gln Val Asn Gly Met Phe Glu Asn Trp Asn Ser
                    645                 650                 655

Asn Gln Phe Val Pro Phe Asn Cys Pro Gln Gln Asp Pro Gln Gln Tyr
                660                 665                 670

Asn Val Phe Thr Asp Leu His Gly Ile Ser Gln Glu Phe Pro Tyr Lys
                675                 680                 685

Ser Glu Met Asp Ser Met Pro Tyr Thr Gln Asn Phe Ile Ser Cys Asn
690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
                740                 745                 750

Asn Pro Gln Ser Ala Ile Ile Thr Pro Gln Thr Cys Tyr Ala Gly Ala
                755                 760                 765

Val Ser Met Tyr Gln Cys Gln Pro Glu Pro Gln His Thr His Val Gly
770                 775                 780

Gln Met Gln Tyr Asn Pro Val Leu Pro Gly Gln Gln Ala Phe Leu Asn
785                 790                 795                 800

Lys Phe Gln Asn Gly Val Leu Asn Glu Thr Tyr Pro Ala Glu Leu Asn
                805                 810                 815

Asn Ile Asn Asn Thr Gln Thr Thr Thr His Leu Gln Pro Leu His His
                820                 825                 830

Pro Ser Glu Ala Arg Pro Phe Pro Asp Leu Thr Ser Ser Gly Phe Leu
                835                 840                 845

<210> SEQ ID NO 4
<211> LENGTH: 134
<212> TYPE: PRT
<213> ORGANISM: Homo sapiens

<400> SEQUENCE: 4

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
                20                  25                  30

Met Ser Leu Leu Tyr Asn Met Asn Asp Cys Tyr Ser Lys Leu Lys Glu
            35                  40                  45

Leu Val Pro Ser Ile Pro Gln Asn Lys Lys Val Ser Lys Met Glu Ile
50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
                100                 105                 110

Leu Ser Leu Gln Ala Ser Glu Phe Pro Ser Glu Leu Met Ser Asn Asp
            115                 120                 125

Ser Lys Ala Leu Cys Gly
            130
```